(12) United States Patent
Hyde et al.

(10) Patent No.: US 8,725,529 B2
(45) Date of Patent: *May 13, 2014

(54) METHODS AND SYSTEMS FOR PRESENTING AN INHALATION EXPERIENCE

(75) Inventors: Roderick A. Hyde, Redmond, WA (US); Robert Langer, Newton, MA (US); Eric C. Leuthardt, St. Louis, MO (US); Robert W. Lord, Seattle, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 753 days.

This patent is subject to a terminal disclaimer.

(21) Appl. No.: 12/378,485

(22) Filed: Feb. 13, 2009

(65) Prior Publication Data

US 2010/0163026 A1    Jul. 1, 2010

Related U.S. Application Data

(63) Continuation-in-part of application No. 12/317,943, filed on Dec. 30, 2008, and a continuation-in-part of application No. 12/319,143, filed on Dec. 31, 2008, and a continuation-in-part of application No. 12/378,284, filed on Feb. 12, 2009.

(51) Int. Cl.
*G06Q 10/00*   (2012.01)
*G06F 19/00*   (2011.01)
*A61M 11/00*   (2006.01)

(52) U.S. Cl.
USPC ................. 705/2; 702/19; 128/200.16

(58) Field of Classification Search
USPC ............................................ 705/2
See application file for complete search history.

(56) References Cited

U.S. PATENT DOCUMENTS

| | | |
|---|---|---|
| 3,946,726 A | 3/1976 | Pikul |
| 4,652,261 A | 3/1987 | Mech et al. |
| 4,784,162 A | 11/1988 | Ricks et al. |
| 4,974,729 A | 12/1990 | Steinnagel |
| 5,071,704 A | 12/1991 | Fischel-Ghodsian |
| 5,455,043 A | 10/1995 | Fischel-Ghodsian |
| 5,458,853 A | 10/1995 | Porter et al. |
| 5,487,378 A | 1/1996 | Robertson et al. |
| 5,546,943 A | 8/1996 | Gould |
| 5,610,674 A | 3/1997 | Martin |

(Continued)

FOREIGN PATENT DOCUMENTS

EP          0328145          8/1989

OTHER PUBLICATIONS

Dog Health: Asthma, http://www.animalhospitals-usa.com/dogs/asthma.html, 2009, Publisher: HarperCollins.

(Continued)

*Primary Examiner* — Hiep V Nguyen

(57) ABSTRACT

Methods, computer program products, and systems are described that include accepting an indication of at least one health-related condition and presenting an indication of at least one artificial sensory experience and an indication of at least one inhalation therapy at least partially based on the accepting at least one indication of a health-related condition.

36 Claims, 33 Drawing Sheets

(56) References Cited

U.S. PATENT DOCUMENTS

| | | | |
|---|---|---|---|
| 5,709,863 | A | 1/1998 | Pageat |
| 5,725,472 | A * | 3/1998 | Weathers ................. 600/21 |
| 5,822,726 | A | 10/1998 | Taylor et al. |
| 5,842,467 | A | 12/1998 | Greco |
| 5,954,641 | A | 9/1999 | Kehr et al. |
| 6,026,807 | A | 2/2000 | Puderbaugh et al. |
| 6,067,523 | A | 5/2000 | Bair et al. |
| 6,168,562 | B1 | 1/2001 | Miller et al. |
| 6,223,744 | B1 | 5/2001 | Garon |
| 6,280,383 | B1 | 8/2001 | Damadian |
| 6,314,384 | B1 | 11/2001 | Goetz |
| 6,315,719 | B1 | 11/2001 | Rode et al. |
| 6,338,338 | B1 | 1/2002 | Brace |
| 6,411,905 | B1 | 6/2002 | Guoliang et al. |
| 6,425,764 | B1 | 7/2002 | Lamson |
| 6,443,153 | B1 | 9/2002 | Viljanen et al. |
| 6,491,643 | B2 | 12/2002 | Katzman et al. |
| 6,500,862 | B1 | 12/2002 | Zanello |
| 6,513,523 | B1 | 2/2003 | Izuchukwu et al. |
| 6,585,519 | B1 | 7/2003 | Jenkins et al. |
| 6,609,068 | B2 | 8/2003 | Cranley et al. |
| 6,647,358 | B2 | 11/2003 | Grass et al. |
| 6,684,880 | B2 | 2/2004 | Trueba |
| 6,780,171 | B2 | 8/2004 | Gabel et al. |
| 6,783,753 | B2 | 8/2004 | Rabinowitz et al. |
| 6,860,239 | B1 | 3/2005 | Begun |
| 6,889,687 | B1 | 5/2005 | Olsson |
| 6,978,212 | B1 | 12/2005 | Sunshine |
| 6,981,502 | B2 | 1/2006 | McCormick et al. |
| 7,044,911 | B2 * | 5/2006 | Drinan et al. ................. 600/300 |
| 7,155,680 | B2 | 12/2006 | Akazawa et al. |
| 7,198,044 | B2 * | 4/2007 | Trueba .................... 128/200.16 |
| 7,353,065 | B2 | 4/2008 | Morrell |
| 7,373,377 | B2 | 5/2008 | Altieri |
| 7,383,837 | B2 | 6/2008 | Robertson et al. |
| 7,427,417 | B2 | 9/2008 | Jendrucko et al. |
| 7,447,541 | B2 | 11/2008 | Huiku et al. |
| 7,720,696 | B1 | 5/2010 | Berger et al. |
| 8,068,983 | B2 | 11/2011 | Vian et al. |
| 2001/0006939 | A1 | 7/2001 | Niven et al. |
| 2001/0034023 | A1 | 10/2001 | Stanton, Jr. et al. |
| 2002/0084996 | A1 | 7/2002 | Temkin et al. |
| 2003/0032638 | A1 | 2/2003 | Kim et al. |
| 2003/0036683 | A1 | 2/2003 | Kehr et al. |
| 2003/0114475 | A1 | 6/2003 | Fox et al. |
| 2004/0107961 | A1 | 6/2004 | Trueba |
| 2004/0116784 | A1 | 6/2004 | Gavish |
| 2004/0254501 | A1 | 12/2004 | Mault |
| 2005/0054942 | A1 | 3/2005 | Melker et al. |
| 2005/0115561 | A1 | 6/2005 | Stahmann et al. |
| 2005/0220843 | A1 | 10/2005 | DeWitt et al. |
| 2006/0031099 | A1 | 2/2006 | Vitello et al. |
| 2006/0058694 | A1 | 3/2006 | Clark et al. |
| 2006/0207596 | A1 | 9/2006 | Lane |
| 2007/0068514 | A1 | 3/2007 | Giroux |
| 2007/0068515 | A1 | 3/2007 | Churchill |
| 2007/0112624 | A1 | 5/2007 | Jung et al. |
| 2007/0123783 | A1 | 5/2007 | Chang |
| 2008/0014566 | A1 | 1/2008 | Chapman et al. |
| 2008/0038701 | A1 | 2/2008 | Booth et al. |
| 2008/0087279 | A1 | 4/2008 | Tieck et al. |
| 2008/0142010 | A1 | 6/2008 | Weaver et al. |
| 2008/0172044 | A1 | 7/2008 | Shelton |
| 2008/0209289 | A1 | 8/2008 | Farnsworth et al. |
| 2008/0230057 | A1 | 9/2008 | Sutherland |
| 2008/0294012 | A1 | 11/2008 | Kurtz et al. |
| 2008/0318913 | A1 | 12/2008 | Fox et al. |
| 2009/0171259 | A1 | 7/2009 | Soerensen et al. |
| 2009/0223249 | A1 | 9/2009 | Julkowski et al. |
| 2009/0306741 | A1 | 12/2009 | Hogle et al. |
| 2011/0226242 | A1 | 9/2011 | Von Hollen et al. |

OTHER PUBLICATIONS

Karen Vail, Chemical and Nonchemical Management of Fleas, 1999, facilities.lipscomb.edu/media.asp?SID=145&UKEY=7743, Published in: US.

Julian R. Yates III, Ctenocephalides felis (Bouche), http://www.extento.hawaii.edu/kbase/urban/site/catflea.htm, , Published in: US, printed Apr. 16, 2009.

Mehlhorn, et al., Effects of Imidacloprid on Adult and Larval Stages of the Flea Ctenocephalides felis After In Vivo and In Vitro Applicat, Parasitology Research, 1999, pp. 625-637, vol. 85, No. 8-9, Published in: US.

Susan Little, Feline Asthma, The Winn Feline Foundation, 2003, http://www.winnfelinehealth.org/health/asthma.html, Published in: US; printed Apr. 16, 2009.

Placerville Veterinary Clinic, Flea Control, www://placervillevet.com/flea_control.htm, 1995-2008, Published in: US.

Cranshaw, et al., Fleas and Plague, http://www.ext.colostate.edu/pubs/insect/05600.html, 2008, Published in: US.

Jeff Feinman, VMD,CVH, Fleas and Ticks, http://www.homevet.com/petcare/fleas.html, 1996-1997, Published in: US.

J.B. Siddall, Insect Growth Regulators and Insect Control: A Critical Appraisal, Environmental Health Perspectives, Apr. 1976, pp. 119-126, vol. 14, Published in: US.

Label Instructions Tightened on Flea & Tick Control Products for Pets, http://www.epa.gov/pesticides/factsheets/hartzq_a.htm, Nov. 2002, Publisher: Environmental Protection Agency, Published in: US.

T. Roy Fukuto, Mechanism of Action of Organophosphorus and Carbamate Insecticides, Environmental Health Perspectives, Jul. 1990, pp. 245-254, vol. 87, Published in: US.

M. Tomizawa, et al., Neonicotinoid Insecticide Toxicology: Mechanisms of Selective Action, Annual Review of Pharmacology and Toxicology, Feb. 2005, pp. 247-268, vol. 45.

Mencke, et al., Therapy and Prevention of Parasitic Insects in Veterinary Medicine Using Imidacloprid, Current Topics in Medicinal Chemistry, Jul. 2002, vol. 2, No. 7.

Hovda, et al., Toxicology of Newer Pesticides for Use in Dogs and Cats, Vet Clin North Am Small Anim. Pract., Mar. 2002, pp. 455-567, vol. 32, No. 2.

U.S. Appl. No. 12/380,013, Hyde et al.
U.S. Appl. No. 12/380,108, Hyde et al.
U.S. Appl. No. 12/380,587, Hyde et al.
U.S. Appl. No. 12/380,679, Hyde et al.
U.S. Appl. No. 12/383,509, Hyde et al.
U.S. Appl. No. 12/383,819, Hyde et al.
U.S. Appl. No. 12/384,104, Hyde et al.
U.S. Appl. No. 12/384,203, Hyde et al.
U.S. Appl. No. 12/386,574, Hyde et al.
U.S. Appl. No. 12/386,669, Hyde et al.
U.S. Appl. No. 12/387,057, Hyde et al.
U.S. Appl. No. 12/387,151, Hyde et al.
U.S. Appl. No. 12/387,321, Hyde et al.
U.S. Appl. No. 12/387,472, Hyde et al.

Harland, C.J. et al.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.

Usmani, Omar S. et al.; "Glucocorticoid Receptor Nuclear Translocation in Airway Cells After Inhaled Combination Therapy"; American Journal of Respiratory and Critical Care Medicine; bearing a date of Apr. 28, 2005; pp. 704-712; vol. 172; located at http://ajrccm.atsjournals.org/cgi/content/abstract/172/6/704 [abstract only].

* cited by examiner

600

Start

610
accepting an indication of a bioactive agent-dispensing inhalation device

620
presenting an indication of an artificial sensory experience at least partially based on accepting an indication of a bioactive agent-dispensing inhalation device Finish

FIG. 6

```
                                600
                                 ↙
                              Start ┌─────────────────────────────────────────────────────────────────────────┐
│ 610                                                                     │
│ accepting an indication of a bioactive agent-dispensing inhalation device│
│ ┌─────────────────────────────────┐ ┌──────────────┐ ┌──────────────┐  │
│ │ 702                             │ │ 706          │ │ 708          │  │
│ │ accepting an indication of a    │ │ accepting an │ │ accepting an │  │
│ │ bioactive agent-dispensing      │ │ indication   │ │ indication   │  │
│ │ inhalation device configured    │ │ of a         │ │ of a         │  │
│ │ to interface with a computing   │ │ bioactive    │ │ bioactive    │  │
│ │ device                          │ │ agent-       │ │ agent-       │  │
│ │ ┌───────────────────────────┐   │ │ dispensing   │ │ dispensing   │  │
│ │ │ 704                       │   │ │ inhalation   │ │ virtual-     │  │
│ │ │ accepting an indication   │   │ │ collar       │ │ reality      │  │
│ │ │ of a bioactive agent-     │   │ │              │ │ headset      │  │
│ │ │ dispensing inhalation     │   │ │              │ │              │  │
│ │ │ device configured to      │   │ │              │ │              │  │
│ │ │ interface wirelessly      │   │ │              │ │              │  │
│ │ │ with a computing device   │   │ │              │ │              │  │
│ │ └───────────────────────────┘   │ │              │ │              │  │
│ └─────────────────────────────────┘ └──────────────┘ └──────────────┘  │
└─────────────────────────────────────────────────────────────────────────┘

┌─────────────────────────────────────────────────────────────────────────┐
│ 620                                                                     │
│ presenting an indication of an artificial sensory experience at least   │
│ partially based on accepting an indication of a bioactive agent-        │
│ dispensing inhalation device                                            │
└─────────────────────────────────────────────────────────────────────────┘

Finish
```

Start

610
accepting an indication of a bioactive agent-dispensing inhalation device

620
presenting an indication of an artificial sensory experience at least partially based on accepting an indication of a bioactive agent-dispensing inhalation device

| 1002 presenting an indication of a prescribed artificial sensory experience |

| 1102 presenting an indication of at least one time period of an expected change in bioactive agent effectiveness | 1104 presenting an indication of at least one time period of an expected change in bioactive agent blood concentration | 1106 recommending an artificial sensory experience administration schedule |

Finish

FIG. 11

```
┌─────────────────────────────────────────────────────────────────────────┐
│ 610                                                                     │
│ accepting an indication of a bioactive agent-dispensing inhalation device│
└─────────────────────────────────────────────────────────────────────────┘
```

```
┌─────────────────────────────────────────────────────────────────────────┐
│ 620                                                                     │
│ presenting an indication of an artificial sensory experience at least partially
│ based on accepting an indication of a bioactive agent-dispensing inhalation
│ device                                                                  │
│  ┌─────────────────────────┐  ┌──────────────┐  ┌──────────────┐        │
│  │ 1202                    │  │ 1206         │  │ 1208         │        │
│  │ utilizing an algorithm for│  │ presenting an│  │ presenting an│        │
│  │ recommending at least one│  │ indication of an│ indication of an│        │
│  │ artificial sensory experience│ │ artificial sensory│ artificial sensory│   │
│  │  ┌───────────────────┐   │  │ experience at │  │ experience at │        │
│  │  │ 1204              │   │  │ least partly │  │ least partly │        │
│  │  │ utilizing an algorithm│  │ based on a  │  │ based on    │        │
│  │  │ configured for identifying a│ │ personal medical│ experimental │        │
│  │  │ contraindication of the│  │ history      │  │ data         │        │
│  │  │ artificial sensory experience│ └──────────────┘  └──────────────┘        │
│  │  └───────────────────┘   │                                         │
│  └─────────────────────────┘                                          │
└─────────────────────────────────────────────────────────────────────────┘
```

Start

610
accepting an indication of a bioactive agent-dispensing inhalation device 620
presenting an indication of an artificial sensory experience at least partially based on accepting an indication of a bioactive agent-dispensing inhalation device

- - - - - - - - - - - - - - - - - - - - - - - - - - - - - -
1502
accepting an indication of an albuterol-dispensing collar configured to be worn proximate to the neck of an individual, accepting a prescribed administration schedule of the albuterol-dispensing collar for the individual, and presenting a prescription for engagement of the individual with a virtual world experience configured to teach the individual a deep breathing technique
- - - - - - - - - - - - - - - - - - - - - - - - - - - - - -

Finish

FIG. 15

METHODS AND SYSTEMS FOR PRESENTING AN INHALATION EXPERIENCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 30, 2008, application Ser. No. 12/317,934, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 31, 2008, application Ser. No. 12/319,143, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 12, 2009, application Ser. No. 12/378,284, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for an inhaled bioactive agent combined with an artificial sensory experience.

SUMMARY

In one aspect, a method includes but is not limited to accepting an indication of at least one health-related condition and presenting an indication of at least one artificial sensory experience and an indication of at least one inhalation therapy at least partially based on the accepting at least one indication of a health-related condition. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting an indication of at least one health-related condition and means for presenting an indication of at least one artificial sensory experience and an indication of at least one inhalation therapy at least partially based on the accepting at least one indication of a health-related condition. In addition to the foregoing, other method aspects are described in the claims, drawings, and text forming a part of the present disclosure.

In one aspect, a system includes but is not limited to circuitry for accepting an indication of at least one health-related condition and circuitry for presenting an indication of at least one artificial sensory experience and an indication of at least one inhalation therapy at least partially based on the accepting at least one indication of a health-related condition. In addition to the foregoing, other method aspects are described in the claims, drawings, and text forming a part of the present disclosure.

In one aspect, a computer program product includes but is not limited to a signal-bearing medium bearing one or more instructions for accepting an indication of at least one health-related condition and one or more instructions for presenting an indication of at least one artificial sensory experience and an indication of at least one inhalation therapy at least partially based on the accepting at least one indication of a health-related condition. In addition to the foregoing, other method aspects are described in the claims, drawings, and text forming a part of the present disclosure.

In one aspect, a system includes but is not limited to a computing device and instructions that when executed on the computing device cause the computing device to accept an indication of at least one health-related condition and present an indication of at least one artificial sensory experience and an indication of at least one inhalation therapy at least partially based on the accepting at least one indication of a health-related condition. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art wilt appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 6 illustrates an operational flow representing example operations related to combining an inhaled bioactive agent and an artificial sensory experience.

FIG. 7 illustrates an alternative embodiment of the operational flow of FIG. 6.

FIG. 11 illustrates an alternative embodiment of the operational flow of FIG. 6.

FIG. 12 illustrates an alternative embodiment of the operational flow of FIG. 6.

FIG. 15 illustrates an alternative embodiment of the operational flow of FIG. 6.

DETAILED DESCRIPTION

Figure 1:
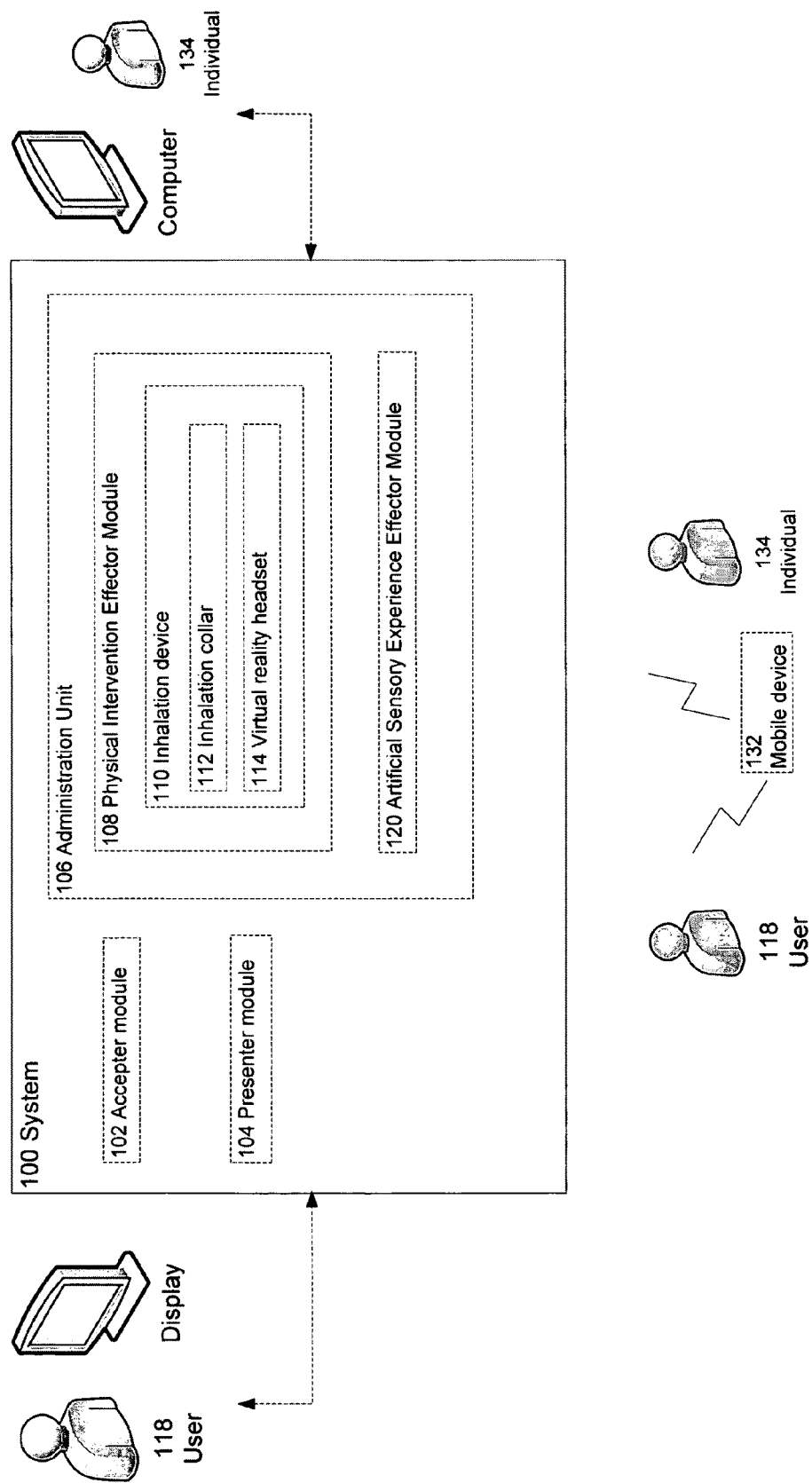
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 3200 may include mobile device 132.

Figure 2:
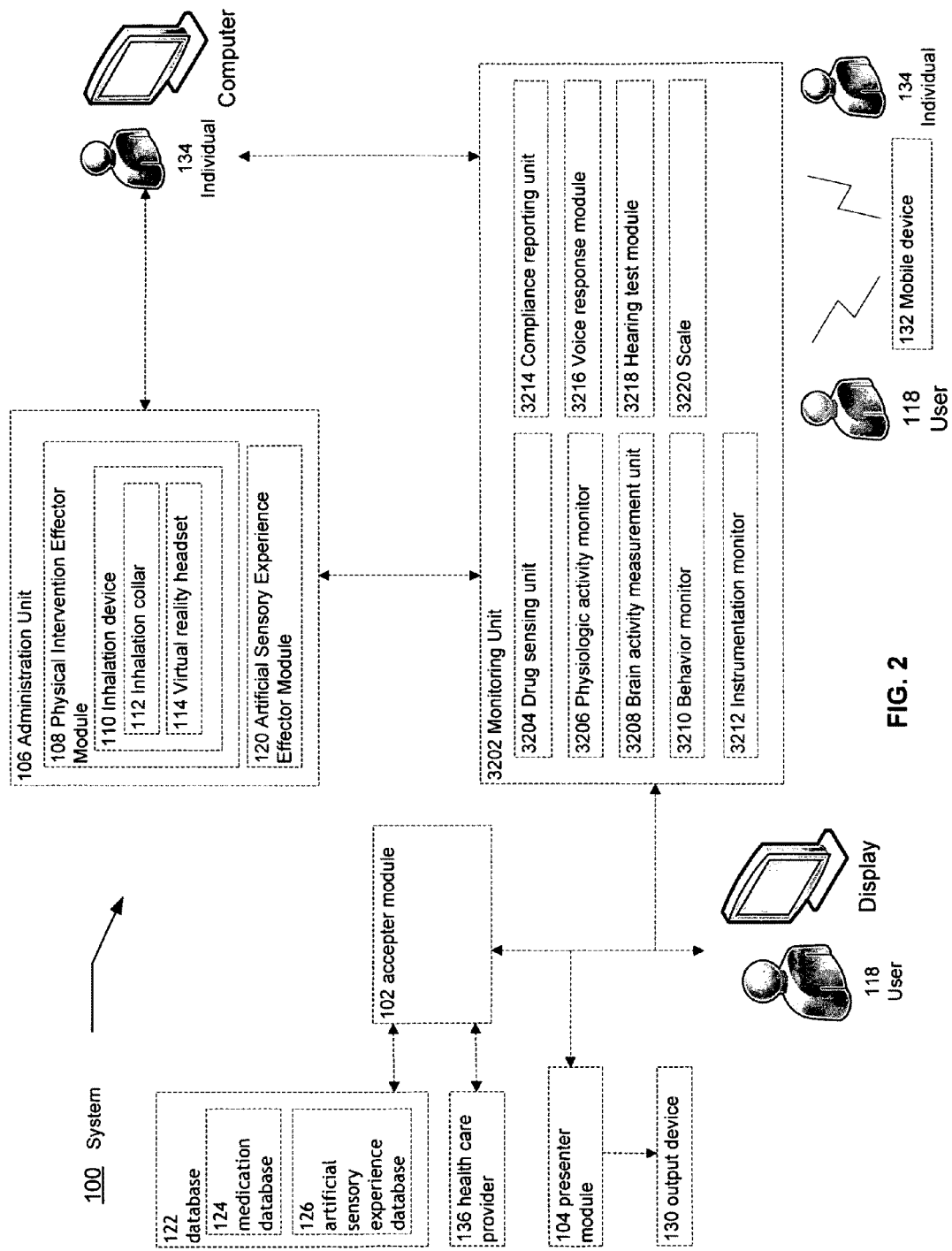
FIG. 2 illustrates an exemplary environment in which one or more technologies may be implemented.

FIG. 2 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, administration unit 106, and/or monitoring unit 3202. Accepter module 102 may receive and/or transmit information and/or data to and/or from user 118, database 122, presenter module 3410, output device 130, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 102, presenter module 104, healthcare provider 136, user 118, individual 134, monitoring unit 3202, and/or administration unit 3222.

Figure 3:
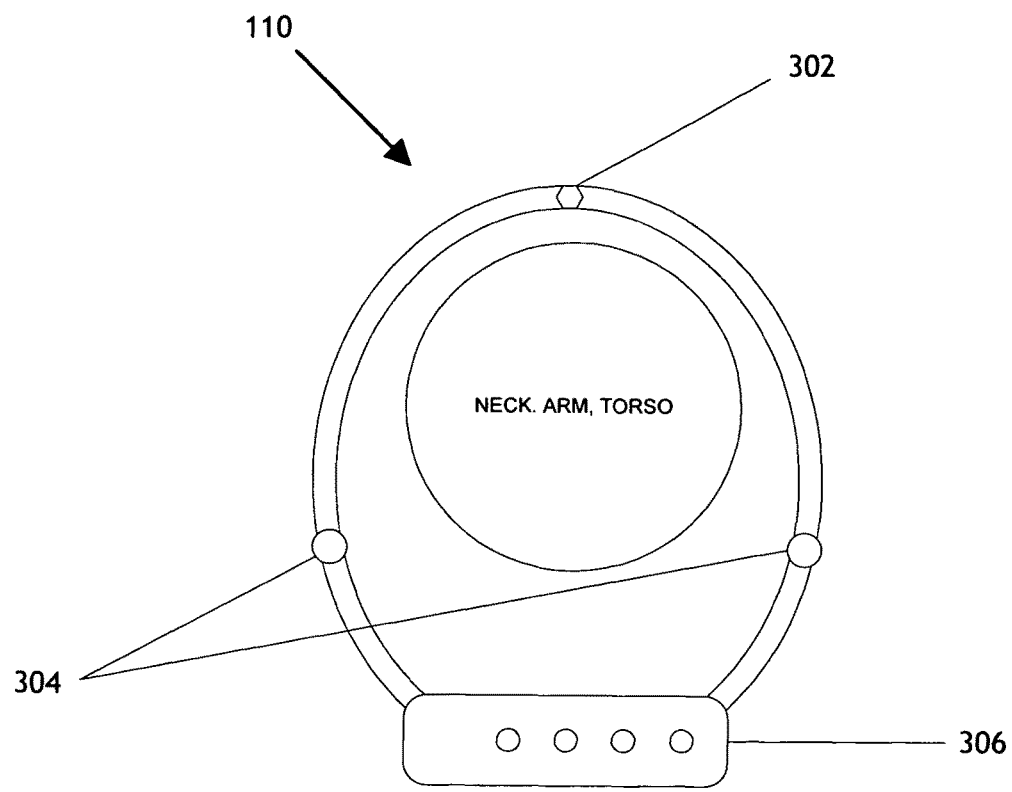
FIG. 3 illustrates an exemplary inhalation device.

FIG. 3 illustrates an exemplary inhalation device 110. An exemplary inhalation device 110 may include a closure device, a transducer, and/or a dispensing reservoir. Inhalation device 110 may include, for example, a collar, a necklace, and/or a bracelet. Inhalation device 110 may include tubing, a chain, a polymer, a metal, a textile, and may be solid and/or hollow. Closure device 302 may include a buckle, Velcro, a snap, a clasp, a lock, a coupler, elastic, and/or magnets. Transducer 304 may include a blood glucose monitor, a blood oxygen monitor, means for sending a signal to a reservoir to dispense medication, such as an antenna, and/or means for powering the unit, such as a battery, memory, and/or a computer processor. Dispensing reservoir 306 may include means for power, such as a battery, means for receiving conditional input, such as a processor and/or memory, and/or means for dispensing a bioactive agent in aerosol, dust and/or vapor form, such as a nebulizer, a sprayer, and/or a nozzle. Additionally, the dispensing reservoir 306 may be removable and/or refillable.

Figure 4:
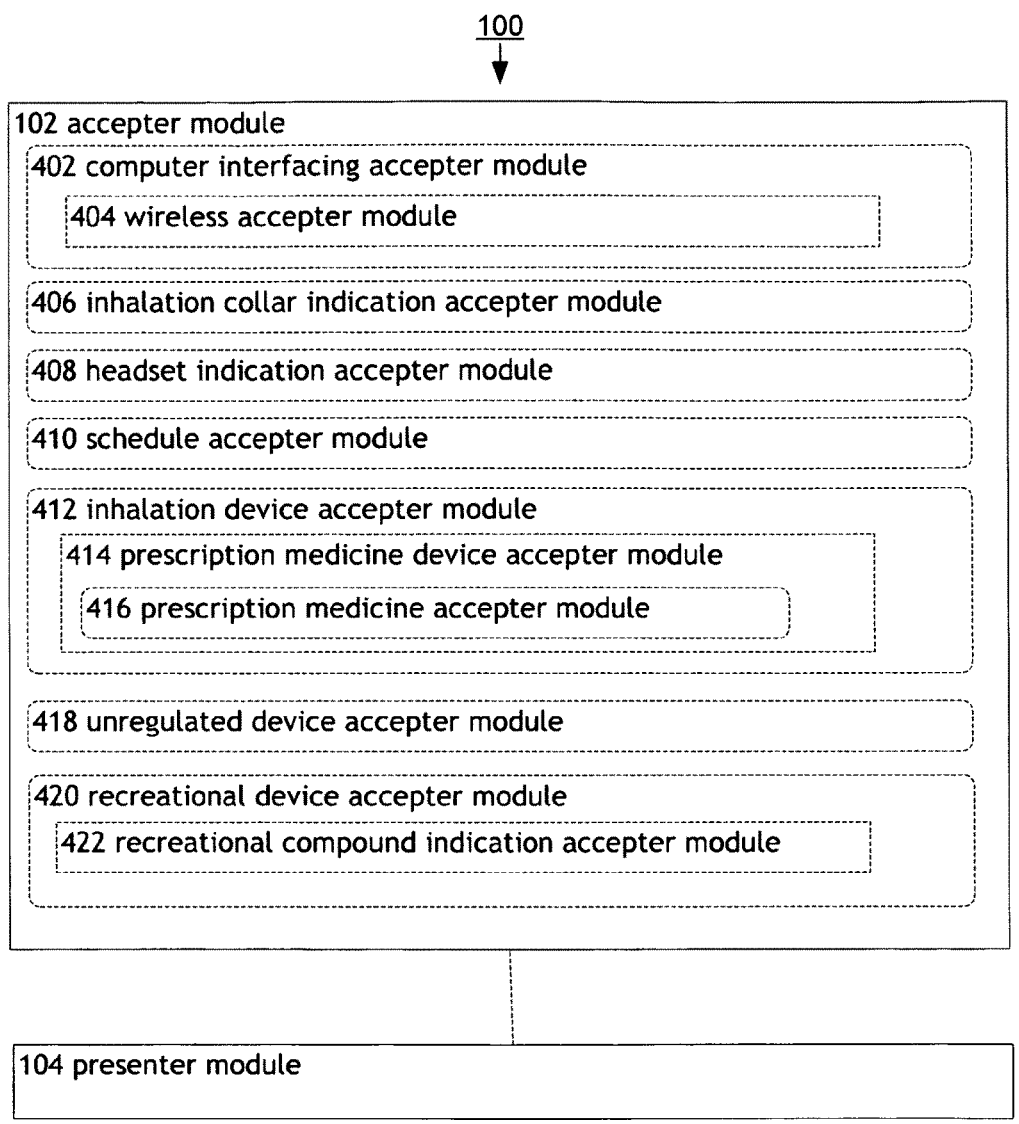
FIG. 4 illustrates an exemplary environment in which one or more technologies may be implemented.

FIG. 4 further illustrates system 100 including accepter module 102 and/or presenter module 104. Accepter module 102 may include computer interfacing accepter module 402, inhalation collar indication accepter module 406, headset indication accepter module 408, schedule accepter module 410, inhalation device accepter module 412, unregulated device accepter module 418, and/or recreational device accepter module 420. Computer interfacing accepter module 402 may include wireless accepter module 404. Inhalation device accepter module 412 may include prescription medicine device accepter module 414 and/or prescription medicine accepter module 416. Recreational device accepter module 420 may include recreational compound indication accepter module 422.

Figure 5:
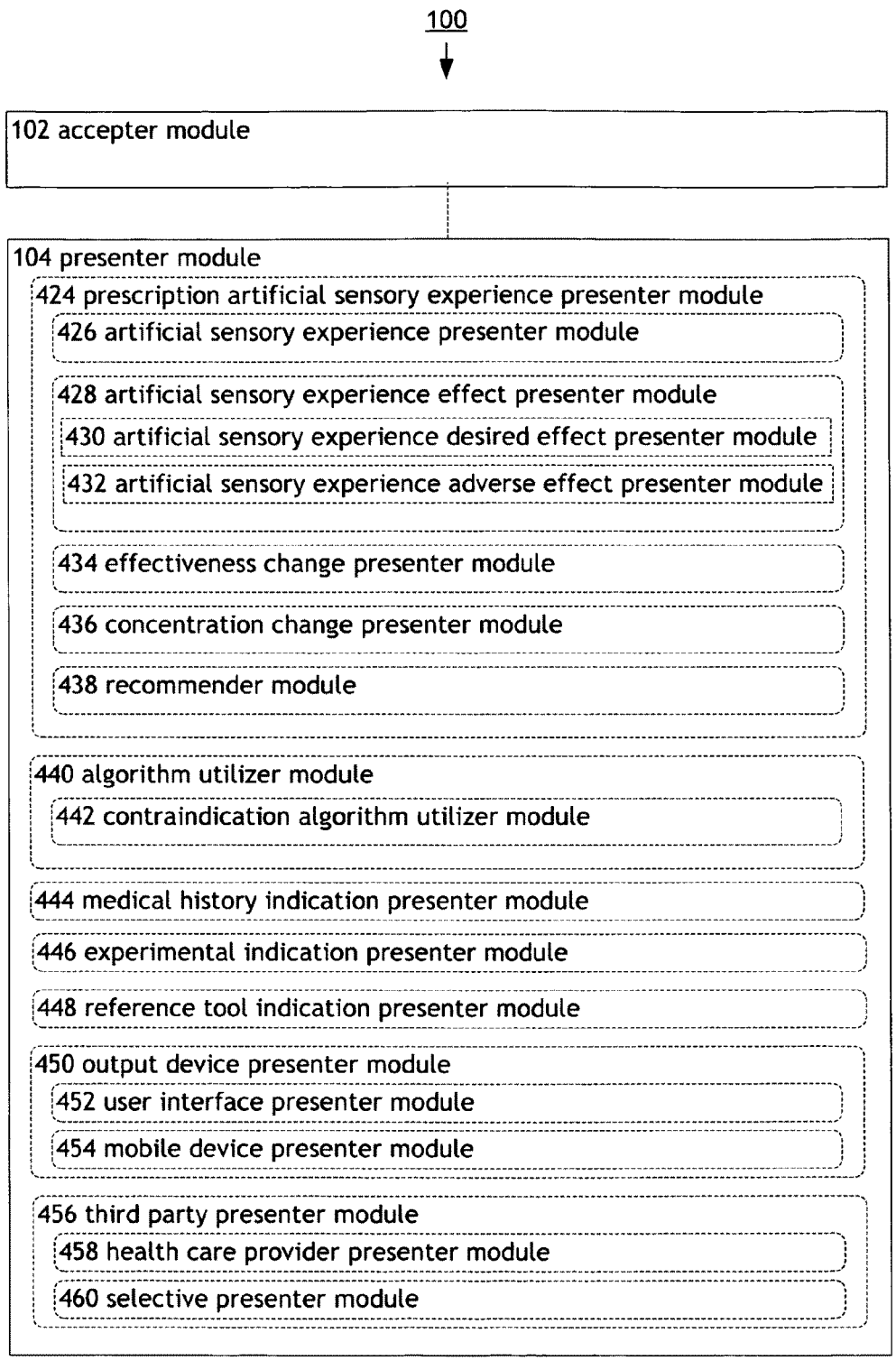
FIG. 5 illustrates an exemplary environment in which one or more technologies may be implemented.

FIG. 5 illustrates system 100 including accepter module 102 and/or presenter module 104. Presenter module 104 may include prescription artificial sensory experience presenter module 424, algorithm utilizer module 440, medical history indication presenter module 444, experimental indication presenter module 446, reference tool indication presenter module 448, output device presenter module 450, and/or third party presenter module 456. Prescription artificial sensory experience presenter module 424 may include artificial sensory experience presenter module 426, artificial sensory experience effect presenter module 428, effectiveness change presenter module 434, concentration change presenter module 436, and/or recommender module 438. Artificial sensory experience effect presenter module 428 may include artificial sensory experience desired effect presenter module 430 and/or artificial sensory experience adverse effect presenter module 432. Algorithm utilizer module 440 may include contraindication algorithm utilizer module 442. Output device presenter module 450 may include user interface presenter module 452 and/or mobile device presenter module 454. Third party presenter module 456 may include health care provider presenter module 458 and/or selective presenter module 460.

FIG. 6 illustrates an operational flow 600 representing example operations related to accepting an indication of at least one health-related condition and presenting an indication of at least one artificial sensory experience and an indication of at least one inhalation therapy at least partially based on the accepting at least one indication of a health-related condition. In FIG. 6 and in following figures that include various examples of operational flows, discussion and explanation may be provided with respect to the above-described examples of FIGS. 1 through 5, and/or with respect to other examples and contexts. However, it should be understood that the operational flows may be executed in a number of other environments and contexts, and/or in modified versions of FIGS. 1 through 5. Also, although the various operational flows are presented in the sequence(s) illustrated, it should be understood that the various operations may be performed in other orders than those which are illustrated, or may be performed concurrently.

After a start operation, the operational flow 600 moves to operation 610. Operation 610 depicts accepting an indication of at least one health-related condition. For example, as shown in FIGS. 1 through 5, accepter module 102 may accept an indication of a bioactive agent-dispensing inhalation device. One example of a bioactive agent-dispensing inhalation device may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, accepter module 102 may accept an indication of a bioactive agent-dispensing collar for dispensing a medication, such as a steroid and/or a bronchodilator. In some instances, accepter module 102 may include a computer processor, a user interface, and/or computer memory.

Then, operation 620 depicts presenting an indication of at least one artificial sensory experience and an indication of at least one inhalation therapy at least partially based on the accepting at least one indication of a health-related condition. For example, as shown in FIGS. 1 through 5, presenter module 104 may present an indication of a virtual world at least partially based on accepting an indication of a bioactive agent-dispensing inhalation device. One example of an artificial sensory experience may include a virtual world and/or other computer-simulated experience. Other examples of an artificial sensory experience may include experiences triggering sight, smell, hearing, touch, and/or taste. For example, presenter module 104 may present an indication of an artificial sensory experience including a virtual scent environment, which may include olfactory stimulation for improving memory. In an additional embodiment, presenter module 104 may present an indication of an artificial sensory experience including a virtual experience where the user is exposed to a virtual mountain environment coupled with a bronchodilator dose from a bioactive agent-dispensing inhalation collar. In this embodiment, the combination bronchodilator and virtual world treatment may serve to help an asthma sufferer to learn effective breathing techniques. Presenting an indication of an artificial sensory experience may include presenting the indication to a physician, to a computer monitor, to a mobile device, and/or to a third party. In some instances, presenter module 104 may include a computer processor and/or a communication device, such as a printer, a computer monitor, and/or a speaker.

FIG. 7 illustrates alternative embodiments of the example operational flow 600 of FIG. 6. FIG. 7 illustrates example embodiments where operation 610 may include at least one additional operation. Additional operations may include operation 702, operation 704, operation 706, and/or operation 708.

Operation 702 illustrates accepting an indication of a health-related physical condition. For example, as shown in FIGS. 1 through 5, computer interfacing accepter module 402 may accept an indication of a bioactive agent-dispensing inhalation device configured to interface with a computing device. In one embodiment, computer interfacing accepter module 402 may accept an indication of a bioactive agent-dispensing inhalation device configured to interface with a virtual game, such as World of Warcraft. Some examples of a computing device may include a personal computer, a virtual-reality helmet and/or headset, and/or a virtual environment. In some instances, computer interfacing accepter module 402 may include a computer processor.

Further, operation 704 illustrates accepting an indication of a bioactive agent-dispensing inhalation device configured to interface wirelessly with a computing device. For example, as shown in FIGS. 1 through 5, wireless accepter module 404 may accept an indication of a bioactive agent-dispensing inhalation device configured to interface wirelessly with a computing device. In one embodiment, wireless accepter module 404 may accept an indication of a wireless inhalation collar configured to interface wirelessly with a computer coupled to wireless video glasses. In this embodiment, both the inhalation collar and the video glasses may be wirelessly connected to the computer. The wireless bioactive agent-dispensing inhalation device may be wirelessly coupled to a computing device using, for example, an IEEE 802.11 computer network and/or a Bluetooth wireless sensor network. One example of wireless video glasses may include Qingbar GP300 video glasses available from 22moo International Pty Ldt., Cabramatta NSW, Australia. In some instances, wireless accepter module 404 may include a computer processor and/or a wireless receiving device, such as a receiving antenna.

Operation 706 illustrates accepting an indication a health-related condition from a medical history. For example, as shown in FIGS. 1 through 5, inhalation collar indication accepter module 406 may accept an indication of a bioactive agent-dispensing inhalation collar. A bioactive agent-dispensing inhalation collar may include a collar with, for example, means for dispensing a bioactive agent, such as a reservoir and/or an accompanying valve and spray nozzle. Additionally, means for dispensing a bioactive agent may include means for dispensing an aerosol, vapor, a powder (e.g. pulmicort and/or foradil), and/or a mist, such as a nebulizer, means for measuring and/or detecting a condition, such as blood oxygen level and/or body temperature, and/or means for processing information, such as a computer processor and/or computer memory. Further, a bioactive agent may be dispensed and/or dispersed in and/or include a surfactant. In one embodiment, inhalation collar indication accepter module 406 may accept an indication of a bioactive agent-dispensing collar having means for dispensing a steroid as an aerosol. Further, a bioactive agent-dispensing inhalation collar may include means for power, such as a battery and/or circuitry for receiving power from an external source, such as an AC adapter power supply. In some instances, inhalation collar indication accepter module 406 may include a computer processor.

Operation 708 illustrates accepting an indication of a bioactive agent-dispensing virtual-reality headset. For example, as shown in FIGS. 1 through 5, headset indication accepter module 408 may accept an indication of a bioactive agent-dispensing virtual-reality headset. A virtual-reality headset may include a microphone, headphones or speakers for hearing, and/or a display. A virtual-reality headset may be configured for enabling a user to engage in an artificial sensory experience including sound, smell, and/or sight. One example of a virtual-reality headset may include a virtual reality helmet configured to give the user a 3600 view of a mountain landscape while dispensing a bronchodilator for helping the user Learn improved breathing techniques. Another example of a virtual reality head set may include an Olympus Eye-Trek FMD-200—TFT active matrix head mounted display with Speaker, available from Olympus America Inc., Center Valley, Pa. In some instances, headset indication accepter module 408 may include a computer processor.

Figure 8:
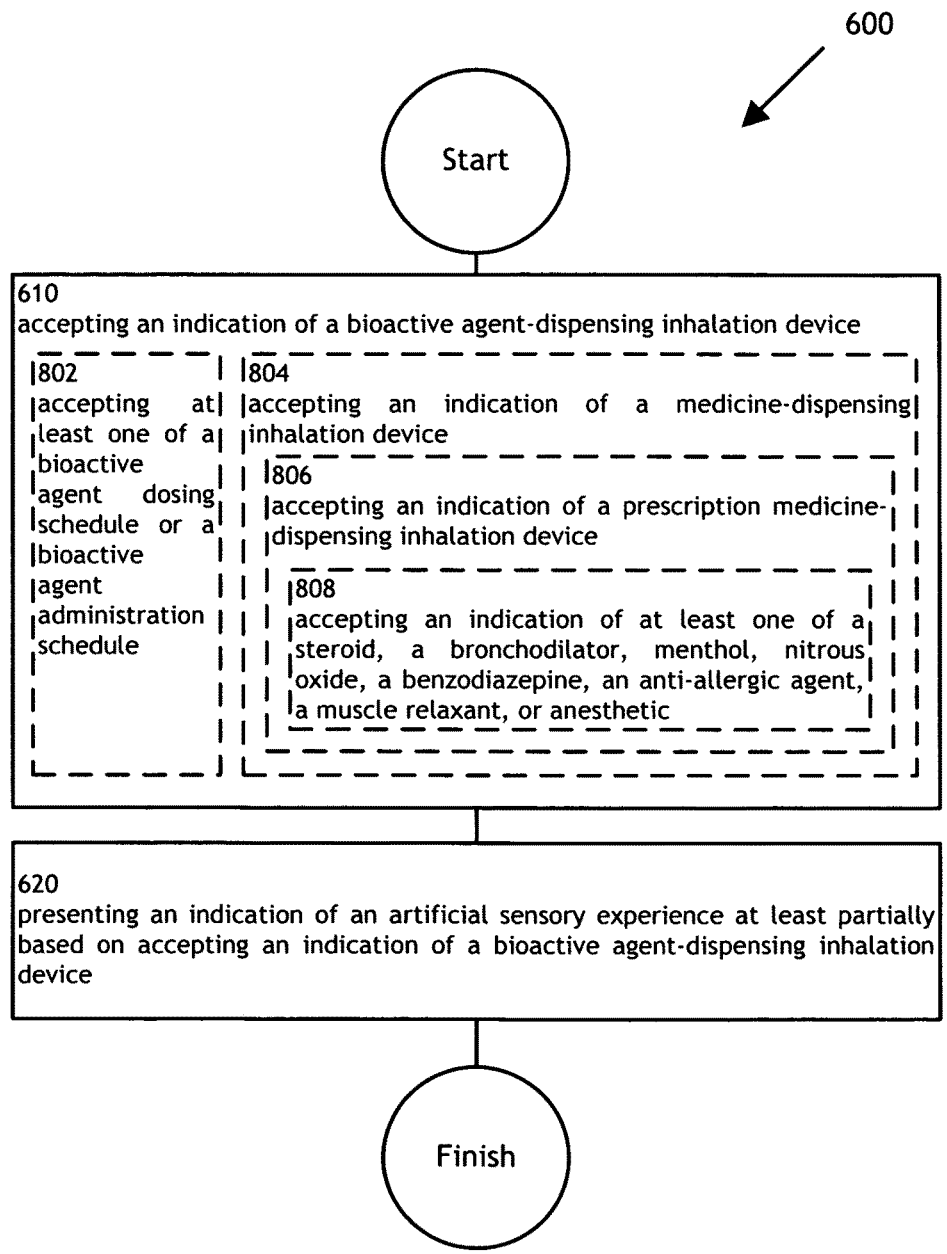
FIG. 8 illustrates an alternative embodiment of the operational flow of FIG. 6.

FIG. 8 illustrates alternative embodiments of the example operational flow 600 of FIG. 6. FIG. 8 illustrates example embodiments where the operation 610 may include at least one additional operation. Additional operations may include an operation 802, an operation 804, an operation 806, and/or an operation 808.

Operation 802 illustrates accepting an indication of a health-related mental condition. For example, as shown in FIGS. 1 through 5, schedule accepter module 410 may accept at least one of a bioactive agent dosing schedule or a bioactive agent administration schedule. Accepting a bioactive agent dosing schedule or a bioactive agent administration schedule may include accepting from a computer processor, accepting from a memory device, and/or accepting from a user input. In one embodiment, schedule accepter module 410 may accept a dosing schedule specifying a bronchodilator administration dosage for a specified time period, such as one dose from an inhalation device once every thirty minutes. In another embodiment, schedule accepter module 410 may accept a bioactive agent administration schedule specifying at least one time a bronchodilator may be administered. In some instances, schedule accepter module 410 may include a computer processor.

Operation 804 illustrates accepting an indication of a medicine-dispensing inhalation device. For example, as shown in FIGS. 1 through 5, inhalation device accepter module 412 may accept an indication of a medicine-dispensing inhalation device. A medicine-dispensing inhalation device may include a device for dispensing a substance for treating a disease and/or illness. For example, a medicine-dispensing inhalation device may include an inhaler as described in Robertson et al., U.S. Pat. No. 7,383,837, which is incorporated herein by reference. Some other examples may include a metered-dose inhaler, a dry powder inhaler, and/or a nebulizer. In one embodiment, inhalation device accepter module 412 may accept an indication of a medicine-dispensing metered-dose inhaler configured to dispense a bronchodilator, such as albuterol. In some instances, inhalation device accepter module 412 may include a computer processor.

Further, operation 806 illustrates accepting an indication of a health-related condition from a user input. For example, as shown in FIGS. 1 through 5, prescription medicine device accepter module 414 may accept an indication of a prescription medicine-dispensing inhalation device. A prescription medicine-dispensing inhalation device may include a device configured to dispense a medication only available from a licensed health care provider. Some examples of a prescription medication available from a licensed health care provider may include a bronchodilator (including beta-agonists and anti-cholinergics), such as albuterol, corticosteroids, nitrous oxide, a sedative, such as benzodiazepine, Theophylline, nedocromil sodium, fluticasone and salmeterol, or combinations thereof. In one embodiment, prescription medicine device accepter module 414 may accept an indication of a prescription medicine-dispensing inhalation device configured for dispensing ciclesonide. In some instances, prescription medicine device accepter module 414 may include a computer processor.

Further, operation 808 illustrates indication of at least one of a prescribed artificial sensory experience or a prescribed inhalation therapy. For example, as shown in FIGS. 1 through 5, prescription medicine accepter module 416 may accept an indication of at least one of a steroid, a bronchodilator, menthol, nitrous oxide, a benzodiazepine, or halothane. One example of a steroid may include an anabolic steroid, which may be a derivative of androgens (such as testosterone), for stimulating growth. Another example of a steroid may include a corticosteroid, which may be often used as an anti-inflammatory prescribed for asthma. A bronchodilator may include a substance that dilates the bronchi and bronchioles decreasing airway resistance and thereby facilitating airflow. A bronchodilator may include a beta-agonist, an anti-cholinergic, and/or a muscle relaxant, such as theophylline. Menthol may include an organic and/or synthetic compound with local anesthetic and counterirritant qualities often used for relieving throat irritation and/or as a decongestant. Nitrous oxide may include a gas often used as a weak general anesthetic. A benzodiazepine may include one class of psychoactive drugs with varying hypnotic, sedative, anxiolytic, anticonvulsant, muscle relaxant and amnesic properties, which may be mediated by slowing down the central nervous system. In one embodiment, prescription medicine accepter module 416 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function and/or decreasing muscle tone. One example of a muscle relaxant may include a methylxanthine, such as Theophylline. An anesthetic may include an inhalational general anesthetic, such as halothane, desflurane, enflurane, isoflurane, and/or sevoflurane. In some instances, prescription medicine accepter module 416 may include a computer processor.

Figure 9:
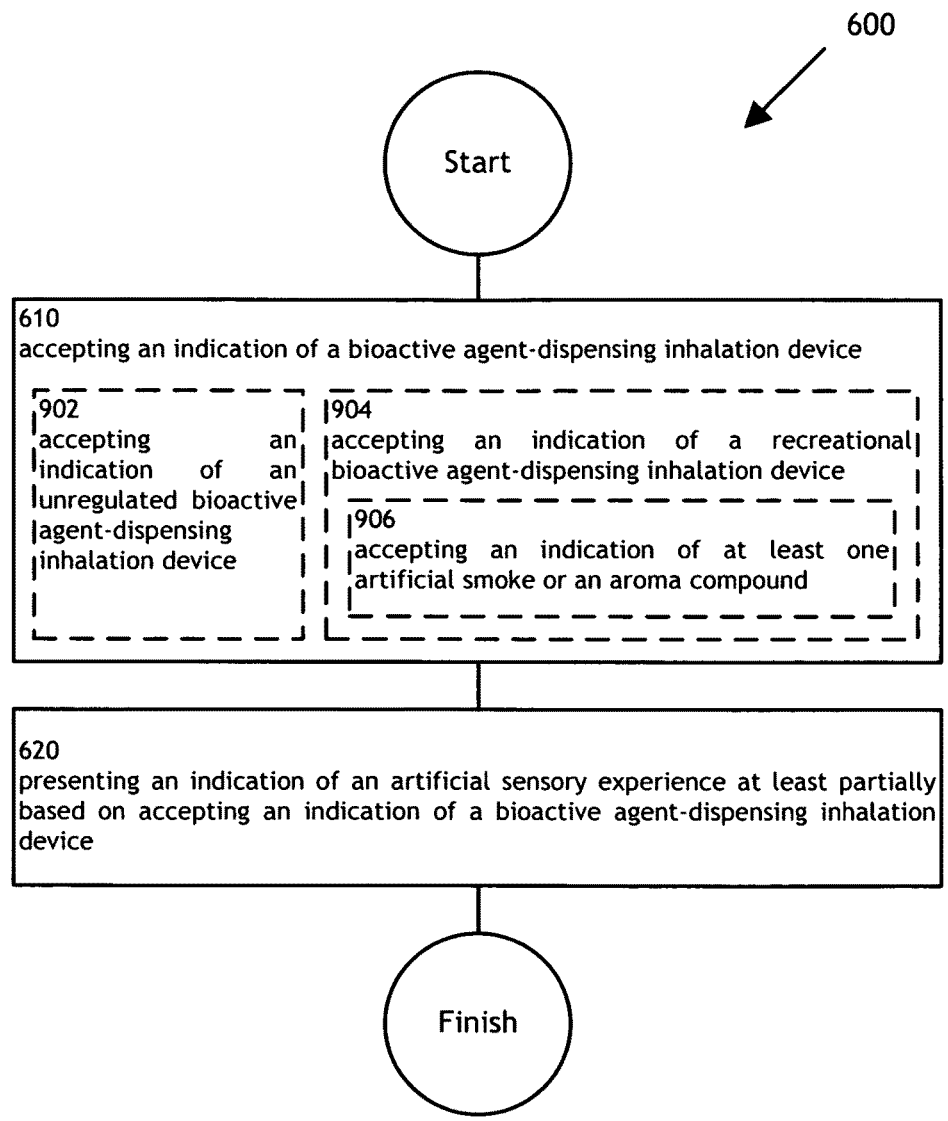
FIG. 9 illustrates an alternative embodiment of the operational flow of FIG. 6.

FIG. 9 illustrates alternative embodiments of the example operational flow 600 of FIG. 6. FIG. 9 illustrates example embodiments where the operation 610 may include at least one additional operation. Additional operations may include an operation 902, an operation 904, and/or an operation 906.

Operation 902 illustrates accepting an indication of an unregulated bioactive agent-dispensing inhalation device. For example, as shown in FIGS. 1 through 5, unregulated device accepter module 418 may accept an indication of an unregulated bioactive agent-dispensing inhalation device. In one embodiment, unregulated device accepter module 418 may accept an indication of an oxygen-dispensing inhalation device. Some examples of an unregulated bioactive agent may include oxygen, aromas used for aromatherapy, and/or menthol. In another embodiment, unregulated device accepter module 418 may accept an indication of an aromatherapeutic-dispensing inhalation collar. In some instances, unregulated device accepter module 418 may include a computer processor.

Operation 904 illustrates accepting an indication of a recreational bioactive agent-dispensing inhalation device. For example, as shown in FIGS. 1 through 5, recreational device accepter module 420 may accept an indication of a recreational bioactive agent-dispensing inhalation device. In one embodiment, recreational device accepter module 420 may accept an indication of a recreational bioactive agent-dispensing inhalation device. Some examples of a recreational bioactive agent may include an aroma compound used for aromatherapy and/or artificial smoke. Other examples of a recreational bioactive agent may include incense and/or smoke, such as incense and/or smoke used in a religious rite. In some instances, recreational device accepter module 420 may include a computer processor.

Further, operation 906 illustrates accepting an indication of at least one artificial smoke or an aroma compound. For example, as shown in FIGS. 1 through 5, recreational compound indication accepter module 422 may accept an indication of at least one artificial smoke or an aroma compound. In one embodiment, recreational compound indication accepter module 422 may accept an indication of artificial smoke while experiencing a virtual world. In another embodiment, recreational compound indication accepter module 422 may accept an indication of lemon oil while experiencing an artificial sensory experience. In this embodiment, the use of lemon oil as an aromatherapeutic may serve to enhance a user's mood and/or provide relaxation. In some instances, recreational compound indication accepter module 422 may include a computer processor.

Figure 10:
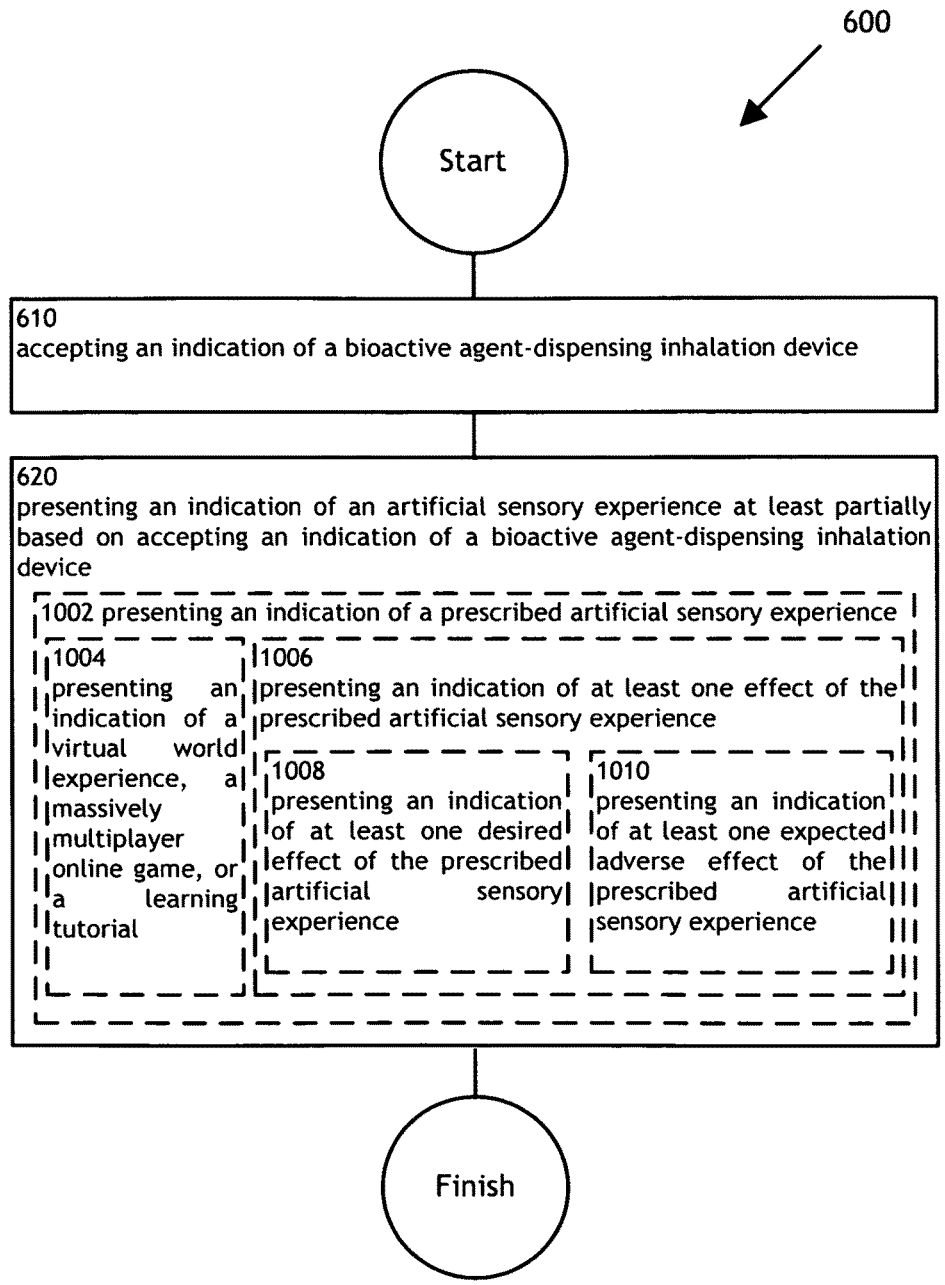
FIG. 10 illustrates an alternative embodiment of the operational flow of FIG. 6.

FIG. 10 illustrates alternative embodiments of the example operational flow 600 of FIG. 6. FIG. 10 illustrates example embodiments where operation 620 may include at least one additional operation. Additional operations may include operation 1002, operation 1004, operation 1006, operation 1008, and/or operation 1010.

Operation 1002 illustrates indication of at least one of a prescribed artificial sensory experience or a prescribed inhalation therapy. For example, as shown in FIGS. 1 through 5, prescription artificial sensory experience presenter module 424 may present an indication of a prescribed artificial sensory experience. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription artificial sensory experience presenter module 424 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. In some instances, prescription artificial sensory experience presenter module 424 may include a computer processor and/or a display device, such as a computer monitor and/or a printer.

Further, operation 1004 illustrates an indication of at least one of a virtual world experience, a massively multiplayer online game, or a learning tutorial. For example, as shown in FIGS. 1 through 5, artificial sensory experience presenter module 426 may present an indication of a virtual world experience, a massively multiplayer online game, or a learning tutorial. A virtual world experience may include a computer-based simulated environment intended to be interactive. Some examples of a virtual world experience may include a text-based chat room, computer conferencing, an online game, a single player game, and/or a computer tutorial. A massively multiplayer online game may include a video game capable of supporting multiple players, such as World of Warcraft and/or SecondLife. Additionally, a massively multiplayer online game may include an experience, such as a game, which may include a video game or other interactive experience involving numbers of individuals, for example, a religious ceremony or combat training exercise. An online learning tutorial may include a screen recording, a written document (either online or downloadable), or an audio file, where a user may be given step by step instructions on how to do something. In one embodiment, artificial sensory experience presenter module 426 may present an indication of a virtual world experience, such as World of Warcraft. In some instances, artificial sensory experience presenter module 426 may include a computer processor.

Further, operation 1006 illustrates indication of at least one effect of the indication of at least one of a prescribed artificial sensory experience. For example, as shown in FIGS. 1 through 5, artificial sensory experience effect presenter module 428 may present an indication of at least one effect of the prescribed artificial sensory experience. In one embodiment, artificial sensory experience effect presenter module 428 may present an indication of at least one effect of the prescribed artificial sensory experience. An effect may include a reaction and/or thing that occurs as a result of the artificial sensory experience. For example, an effect may include a side effect, a desired effect, and/or an adverse effect. Some examples of an effect may include an increased bioactive agent efficacy, dizziness, and/or a decreased heart rate. In some instances, artificial sensory experience effect presenter module 428 may include a computer processor.

Further, operation 1008 illustrates presenting an indication of at least one expected desired effect of at least one desired effect of the prescribed artificial sensory experience. For example, as shown in FIGS. 1 through 5, artificial sensory experience desired effect presenter module 430 may present an indication of at least one desired effect of the prescribed artificial sensory experience. Some examples of a desired effect may include effects such as an increased bioactive agent efficacy, a cured illness and/or condition, and/or a changed behavior. In one embodiment, artificial sensory experience desired effect presenter module 430 may present an indication of an increased opioid efficacy measured by self pain evaluation by an individual. In some instances, artificial sensory experience desired effect presenter module 430 may include a computer processor and/or a display, such as a monitor and/or a printer.

Further, operation 1010 illustrates an indication of at least one prescribed inhalation therapy. For example, as shown in FIGS. 1 through 5, artificial sensory experience adverse effect presenter module 432 may present an indication of an expected adverse effect of the prescribed artificial sensory experience. An adverse effect may include a harmful and/or undesired effect resulting from an intervention, such as an artificial sensory experience. Some examples of an adverse effect may include headache, dizziness, depression, bleeding, seizure, and/or fever. In one embodiment, artificial sensory experience adverse effect presenter module 432 may present an indication of fever in an individual while being administered a prescribed artificial sensory experience and bioactive agent. In some instances, artificial sensory experience adverse effect presenter module 432 may include a computer processor, a display device, such as a monitor and/or printer, and/or medical instrumentation, such as a thermometer configured for measuring a body temperature.

FIG. 11 illustrates alternative embodiments of the example operational flow 600 of FIG. 6. FIG. 11 illustrates example embodiments where operation 620 may include at least one additional operation. Additional operations may include operation 1102, operation 1104, and/or operation 1106.

Operation 1102 illustrates an indication of at least one prescribed bioactive agent. For example, as shown in FIGS. 1 through 5, effectiveness change presenter module 434 may present an indication of at least one time period of an expected change in bioactive agent effectiveness. In one embodiment, effectiveness change presenter module 434 may present an indication of a time period when an opioid is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, effectiveness change presenter module 434 may present an indication of a time period where a blood stream morphine concentration drops. This time period of low blood stream morphine concentration may be appropriate for presenting an immersive virtual world for serving as a distraction to any increase in pain caused by lowered morphine concentration. In some instances, effectiveness change presenter module 434 may include a computer processor.

Further, operation 1104 illustrates an indication of at least one time period of an expected change in bioactive agent blood concentration. For example, as shown in FIGS. 1 through 5, concentration change presenter module 436 may present an indication of at least one time period of an expected change in bioactive agent blood concentration. In one embodiment, concentration change presenter module 436 may present an indication of a one hour time period of an expected change in hydrocodone blood concentration. Indicating a time period of a change in blood concentration may serve to help determine an artificial sensory experience administration schedule. For example, if a bioactive agent blood concentration is expected to be reduced during a certain time period, an artificial sensory experience configured for distracting an individual from pain may be selected for administration during that time period. In some instances, concentration change presenter module 436 may include a computer processor and/or a display device, such as a printer and/or a computer monitor.

Further, operation 1106 illustrates recommending at least one of an artificial sensory experience administration schedule. For example, as shown in FIGS. 1 through 5, recommender module 438 may recommend an artificial sensory experience administration schedule. In one embodiment, recommender module 438 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In some instances, recommender module 438 may include a computer processor.

FIG. 12 illustrates alternative embodiments of the example operational flow 600 of FIG. 6. FIG. 12 illustrates example embodiments where operation 620 may include at least one additional operation. Additional operations may include operation 1202, operation 1204, operation 1206, and/or operation 1208.

Operation 1202 illustrates utilizing an algorithm for recommending at least one artificial sensory experience. For example, as shown in FIGS. 1 through 5, algorithm utilizer module 440 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 440 may utilize an algorithm that uses an inputted indication of an analgesic, such as oxycodone, and determines a suitable artificial sensory experience by analyzing periods of low blood concentration of the oxycodone. In this embodiment, algorithm utilizer module 440 may recommend an artificial sensory experience that may be effective in pain distraction when bioactive agent blood concentration may be reduced but before an additional dose may be available. In some instances, algorithm utilizer module 440 may include a computer processor.

Further, operation 1204 illustrates utilizing an algorithm configured for identifying a contraindication of the artificial sensory experience. For example, as shown in FIGS. 1 through 5, contraindication algorithm utilizer module 442 may utilize an algorithm configured for identifying a contraindication of the artificial sensory experience. A contraindication of an artificial sensory experience may include giving an indication against the advisability of the artificial sensory experience. For example, contraindication algorithm utilizer module 442 may utilize an algorithm that considers an individual's personal medical history, such as a phobia, and may recommend not prescribing a certain artificial sensory experience, which may include an object that may trigger the phobia. Contraindication algorithm utilizer module 442 may identify a contraindication of an artificial sensory experience for reasons such as an adverse effect and/or inefficacy. In some instances, contraindication algorithm utilizer module 442 may include a computer processor.

Operation 1206 illustrates presenting an indication of an artificial sensory experience at least partly based on a personal medical history. For example, as shown in FIGS. 1 through 5, medical history indication presenter module 444 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history indication presenter module 444 may present an indication of a suitable virtual world based on a personal medical history. In this embodiment, the personal medical history may indicate that an individual may be averse to a certain virtual world, such as a virtual world with rapid animation that may cause nausea. In some instances, medical history indication presenter module 444 may include a computer processor and/or a display device, such as a computer monitor and/or a printer.

Operation 1208 illustrates utilizing an algorithm configured for recommending at least one of an artificial sensory experience. For example, as shown in FIGS. 1 through 5, experimental data indication presenter module 446 may present an indication of an artificial sensory experience at least partly based on experimental data. Experimental data may include any data from an experiment, such as a clinical trial. The experiment may be an experiment including an individual and/or a group of people. In one embodiment, experimental data indication presenter module 446 may present an indication of a virtual world suitable for an individual based on a clinical trial involving a group of 1,000 people showing a certain success rate for reducing a phobia, such as fear of heights. In some instances, experimental data indication presenter module 446 may include a computer processor and/or a display device, such as a computer monitor, a mobile phone, and/or a printer.

Figure 13:
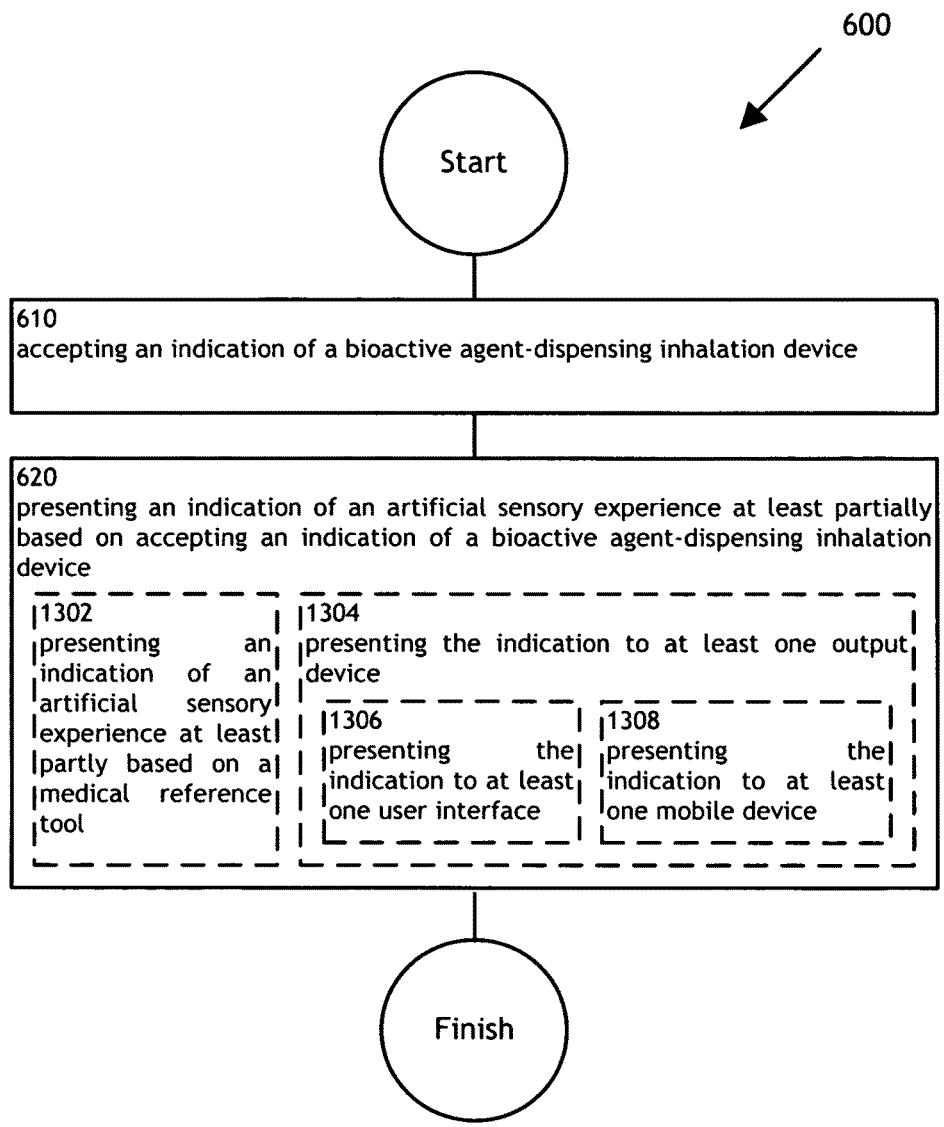
FIG. 13 illustrates an alternative embodiment of the operational flow of FIG. 6.

FIG. 13 illustrates alternative embodiments of the example operational flow 600 of FIG. 6. FIG. 13 illustrates example embodiments where the operation 620 may include at least one additional operation. Additional operations may include an operation 1302, an operation 1304, an operation 1306, and/or an operation 1308.

Operation 1302 illustrates presenting at least one of an indication of an artificial sensory experience or an indication of inhalation therapy at least partly based on a medical reference tool. For example, as shown in FIGS. 1 through 5, reference tool indication presenter module 448 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, reference tool indication presenter module 448 may present an indication of an artificial sensory experience based on a reference database, such as a database including data from a clinical trial. In some instances, reference tool indication presenter module 448 may include a computer processor and/or a display device, such as a mobile phone, a printer, and/or a computer monitor.

Operation 1304 illustrates presenting the indication to at least one output device. For example, as shown in FIGS. 1 through 5, output device presenter module 450 may present to at least one output device. In one example, output device presenter module 450 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 450 may include a computer processor.

Further, operation 1306 illustrates presenting the indication to at least one user interface. For example, as shown in FIGS. 1 through 5, user interface presenter module 452 may present to at least one user interface. In one embodiment, user interface presenter module 452 may present to a touchscreen device. A user interface may include means by which an individual may interact with a system. Some examples of a user interface may include a touchscreen, a graphical user interface, a tactile interface, and/or a live user interface. In some instances, user interface presenter module 452 may include a computer processor.

Further, operation 1308 illustrates presenting the indication to at least one mobile device. For example, as shown in FIGS. 1 through 5, mobile device presenter module 454 may present to at least one mobile device. In one embodiment, mobile device presenter module 454 may present to a mobile phone. A mobile device may include a portable computing device and may have wireless connection capability. Some examples of a mobile device may include a laptop or notebook computer, a personal digital assistant (PDA), an iPod, a smartphone, an Enterprise digital assistant (EDA), and/or a pager. In some instances, mobile device presenter module 454 may include a computer processor.

Figure 14:
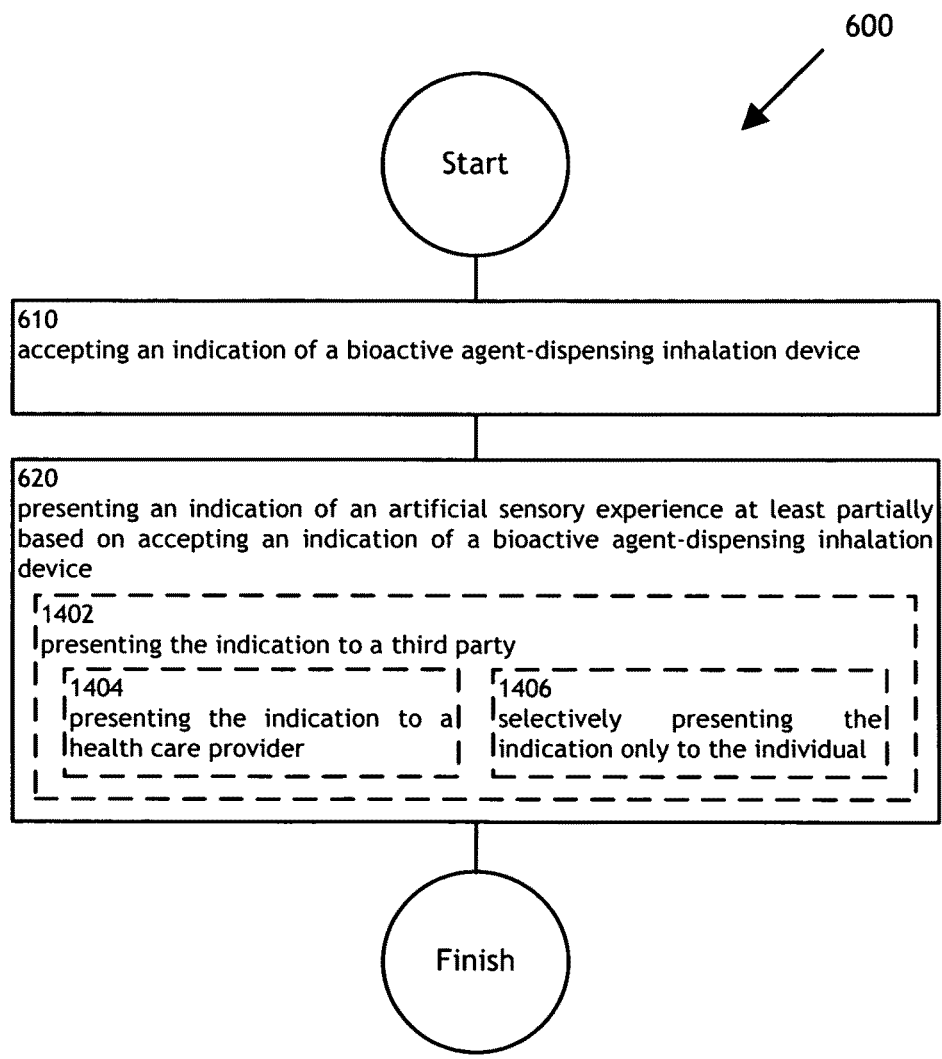
FIG. 14 illustrates an alternative embodiment of the operational flow of FIG. 6.

FIG. 14 illustrates alternative embodiments of the example operational flow 600 of FIG. 6. FIG. 14 illustrates example embodiments where operation 620 may include at least one additional operation. Additional operations may include operation 1402, operation 1404, and/or operation 1406.

Operation 1402 illustrates presenting the indication to at least one third party. For example, as shown in FIGS. 1 through 5, third party presenter module 456 may present to an individual's physician. A third party may include a party that is an independent party, person, and/or entity. Some examples of a third party may include a physician, a medical database, a hospital, a law enforcement agency, and/or a pharmacy. In one embodiment, third party presenter module 456 may present an indication to an insurance company. Another example of reporting to a third party may include creating displays and reports for aggregating data from therapy results, further discussed in Bair et al., U.S. Pat. No. 6,067,523, which is incorporated herein by reference. In some instances, third party presenter module 456 may include a computer processor and/or a communications device, such as a monitor and network link.

Further, operation 1404 illustrates presenting the indication to at least one health care provider. For example, as shown in FIGS. 1 through 5, health care provider presenter module 458 may present to a health care provider. A health care provider may include a pharmacy, a pharmaceutical company, a medical device company, a research institution, a computer software and/or computer hardware company, a website, a nurse and/or a physician. In one embodiment, health care provider presenter module 458 may present to a physician a prescribed combination artificial sensory experience and bioactive agent therapy via a secured website. In some instances, health care provider presenter module 458 may include a computer processor.

Further, operation 1406 illustrates selectively presenting the indication only to the individual. For example, as shown in FIGS. 1 through 5, selective presenter module 460 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 460 may present only to individual 134 and may keep results of a certain combination therapy confidential. In one embodiment, an encryption key may be employed to protect selected information. In an additional example, selective presenter module 460 may report only to a law enforcement agency and/or representative, such as a probation officer, and not to individual 134. In some instances, selective presenter module 460 may include a computer processor.

FIG. 15 illustrates alternative embodiments of the example operational flow 600 of FIG. 6. FIG. 15 illustrates example embodiments where the operation 620 may include at least one additional operation. Additional operations may include an operation 1502.

Operation 1502 illustrates accepting an indication of an individual's asthma, presenting a prescribed administration schedule of an albuterol-dispensing collar therapy for the individual, and presenting a prescription for engagement of the individual with a virtual world experience configured to teach the individual a deep breathing technique. For example, as shown in FIGS. 1 through 5, accepter module 102 and/or presenter module 104 may accept an indication of an albuterol-dispensing collar configured to be worn proximate to the neck of an individual, accept a prescribed administration schedule of the albuterol-dispensing collar for the individual, and present a prescription for engagement of the individual with a virtual world experience configured to teach the individual a deep breathing technique. In some instances, accepter module 102 and/or presenter module 104 may include a computer processor.

Figure 16:
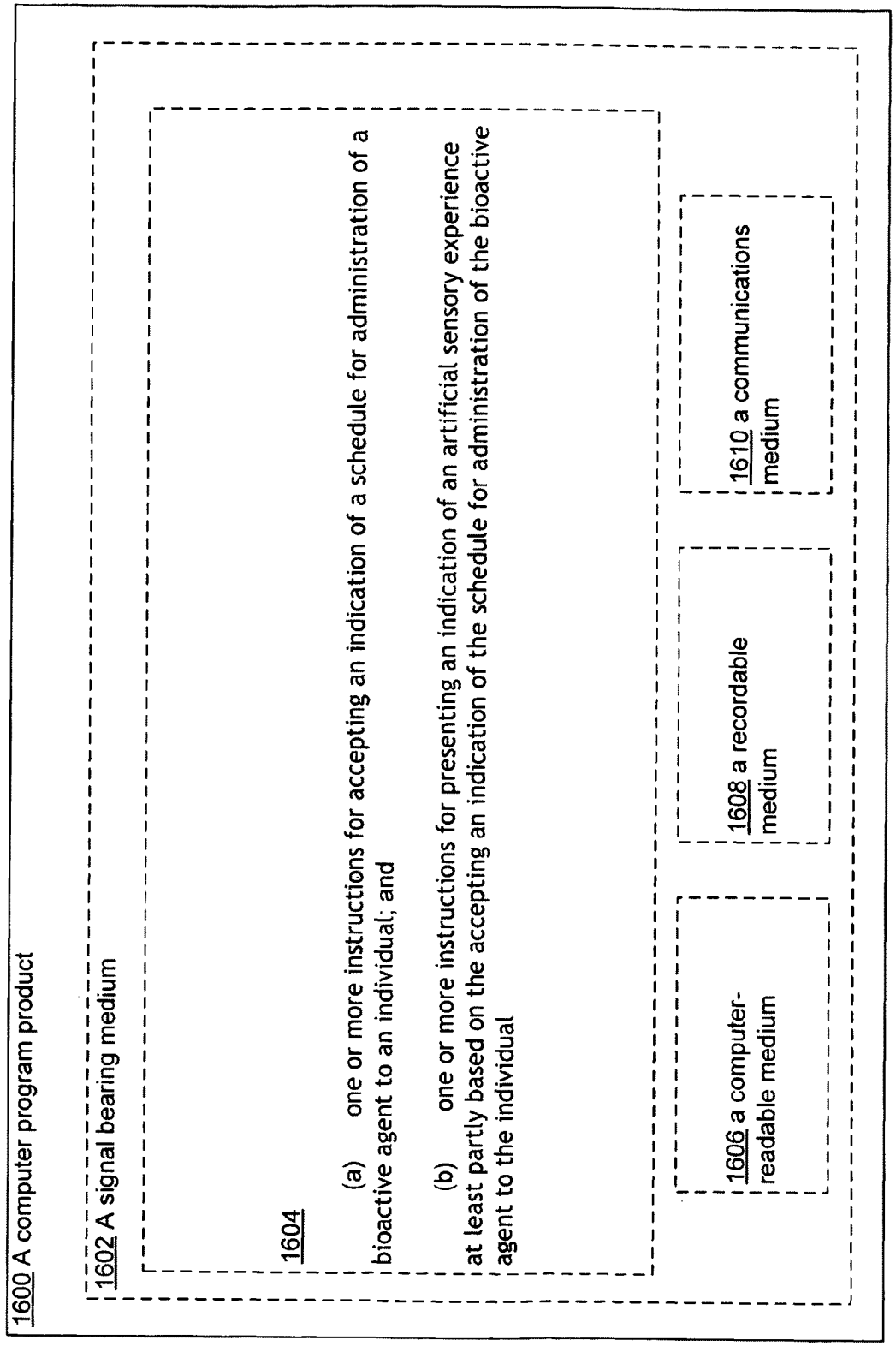
FIG. 16 illustrates a computer program product related to combining an inhaled bioactive agent and an artificial sensory experience.

FIG. 16 illustrates a partial view of an example computer program product 1600 that includes a computer program 1604 for executing a computer process on a computing device. An embodiment of the example computer program product 1600 is provided using a signal-bearing medium bearing 1602, and may include one or more instructions for accepting an indication of at least one health-related condition and one or more instructions for presenting an indication of at least one artificial sensory experience and an indication of at least one inhalation therapy at least partially based on the accepting at least one indication of a health-related condition. The one or more instructions may be, for example, computer executable and/or logic-implemented instructions. In one implementation, the signal-bearing medium 1602 may include a computer-readable medium 1606. In one implementation, the signal bearing medium 1602 may include a recordable medium 1608. In one implementation, the signal bearing medium 1602 may include a communications medium 1610.

Figure 17:
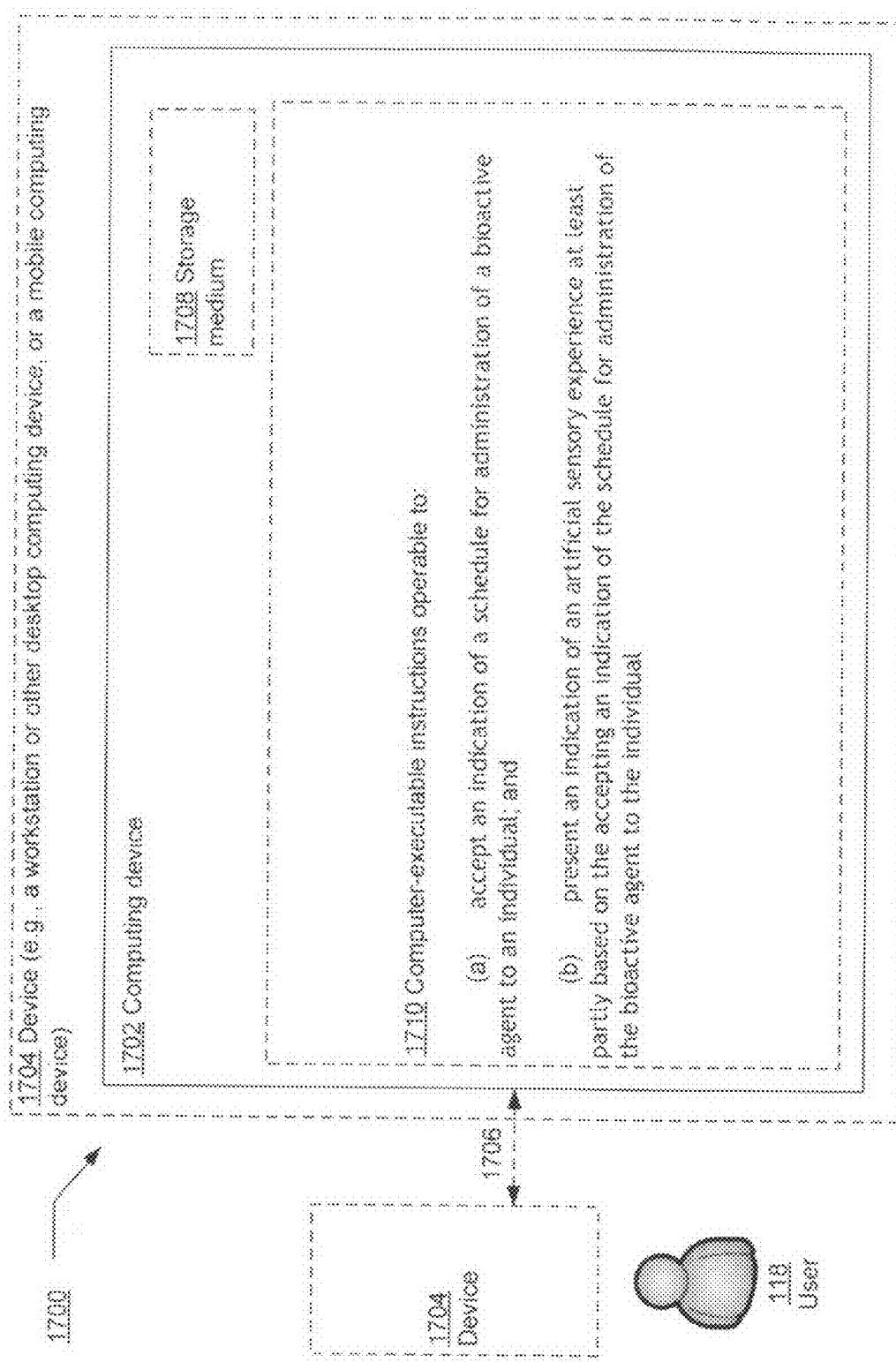
FIG. 17 illustrates a system related to combining an inhaled bioactive agent and an artificial sensory experience.

FIG. 17 illustrates an example system 1700 in which embodiments may be implemented. The system 1700 includes a computing system environment. The system 1700 also illustrates the user 118 using a device 1704, which is optionally shown as being in communication with a computing device 1702 by way of an optional coupling 1706. The optional coupling 1706 may represent a local, wide-area, or peer-to-peer network, or may represent a bus that is internal to a computing device (e.g., in example embodiments in which the computing device 1702 is contained in whole or in part within the device 1704). A storage medium 1708 may be any computer storage media.

The computing device 1702 includes computer-executable instructions 1710 that when executed on the computing device 1702 cause the computing device 1702 to accept an indication of a schedule for administration of a bioactive agent to an individual and present an indication of an artificial sensory experience at least partly based on the accepting an indication of the schedule for administration of the bioactive agent to the individual. As referenced above and as shown in FIG. 17, in some examples, the computing device 1702 may optionally be contained in whole or in part within the device 1704.

In FIG. 17, then, the system 1700 includes at least one computing device (e.g., 1702 and/or 1704). The computer-executable instructions 1710 may be executed on one or more of the at least one computing device. For example, the computing device 1702 may implement the computer-executable instructions 1710 and output a result to (and/or receive data from) the computing device 1704. Since the computing device 1702 may be wholly or partially contained within the computing device 1704, the device 1704 also may be said to execute some or all of the computer-executable instructions 1710, in order to be caused to perform or implement, for example, various ones of the techniques described herein, or other techniques.

The device 1704 may include, for example, a portable computing device, workstation, or desktop computing device. In another example embodiment, the computing device 1702 is operable to communicate with the device 1704 associated with the user 118 to receive information about the input from the user 118 for performing data access and data processing and presenting an output of the user-health test function at least partly based on the user data.

Figure 18:
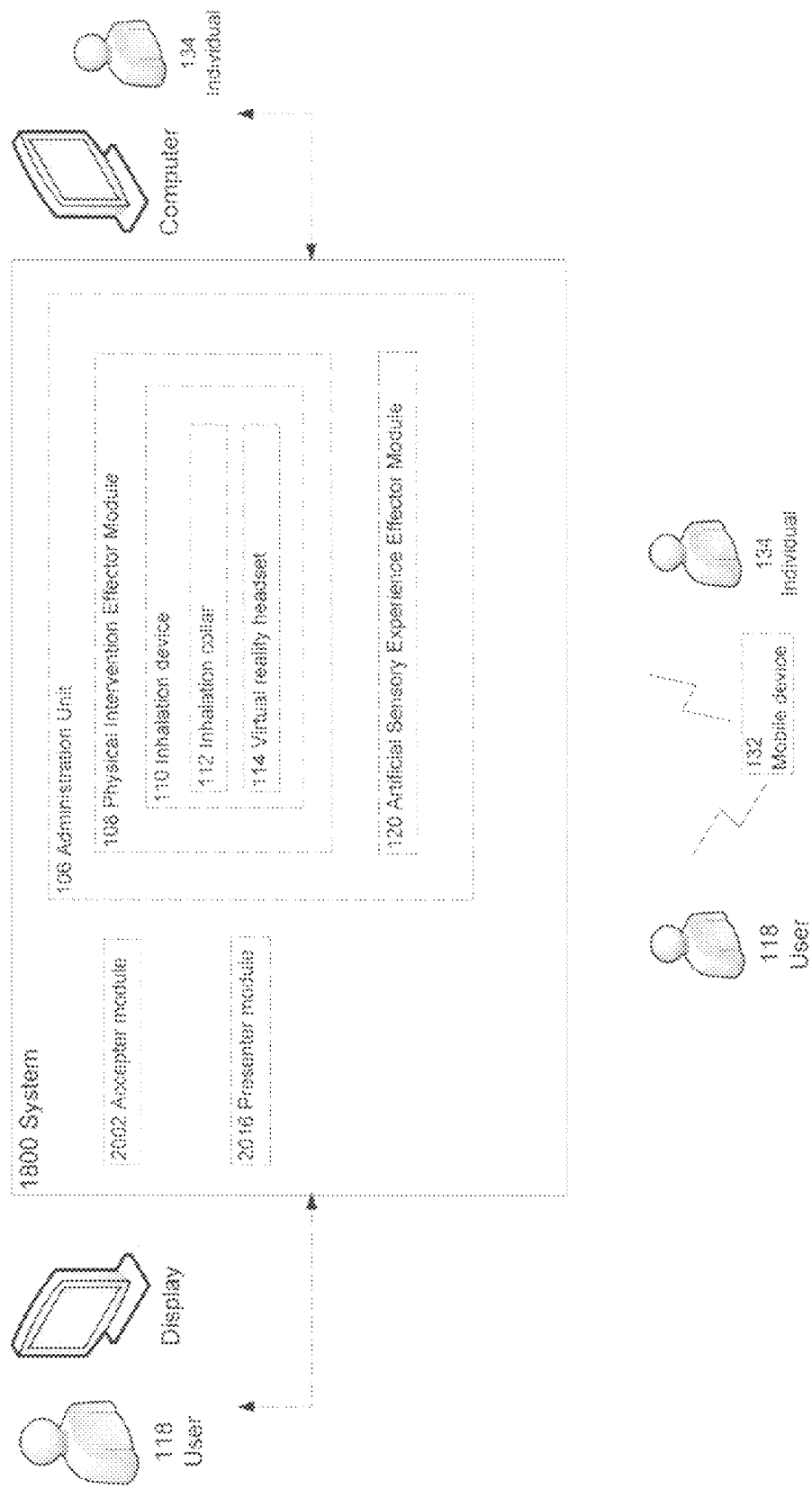
FIG. 18 illustrates an exemplary environment in which one or more technologies may be implemented.

FIG. 18 illustrates system 1800 for accepting an indication of at least one health-related condition and/or presenting an indication of at least one artificial sensory experience and an indication of at least one inhalation therapy at least partially based on the accepting at least one indication of a health-related condition. System 1800 may include accepter module 2002, presenter module 2016, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 1800 may include mobile device 132.

Figure 19:
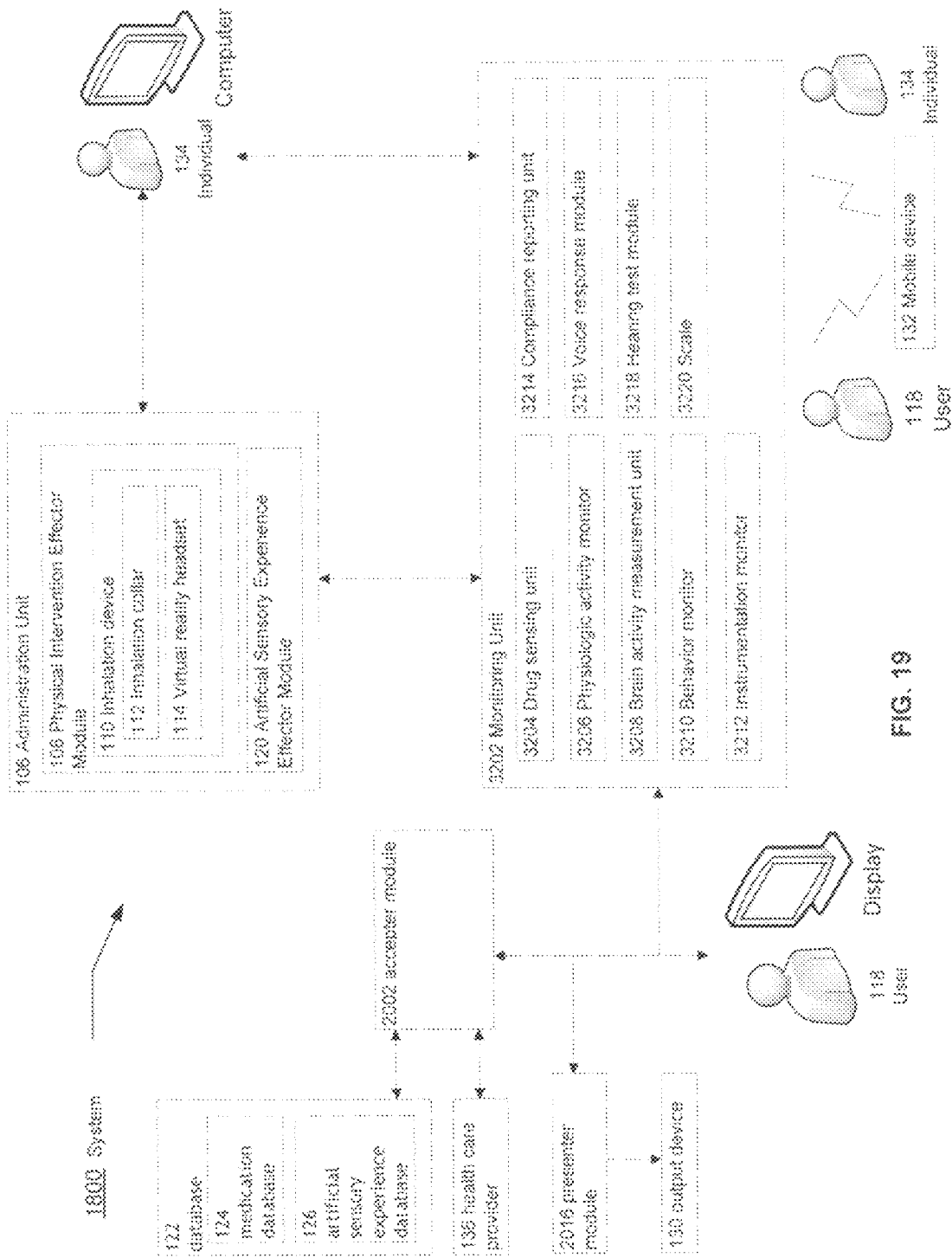
FIG. 19 illustrates an exemplary environment in which one or more technologies may be implemented.

FIG. 19 illustrates system 1800 for accepting an indication of at least one health-related condition and/or presenting an indication of at least one artificial sensory experience and an indication of at least one inhalation therapy at least partially based on the accepting at least one indication of a health-related condition. System 1800 may include accepter module 2002, presenter module 2016, administration unit 106, and/or monitoring unit 3202. Accepter module 2002 may receive and/or transmit information and/or data to and/or from user 118, database 122, presenter module 2016, output device 130, and/or health care provider 136. A user may include individual 134, health care provider 136, a patient, and/or another affected person or entity. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 102, presenter module 104, healthcare provider 136, user 118, individual 134, monitoring unit 3202, and/or administration unit 3222.

Figure 20:
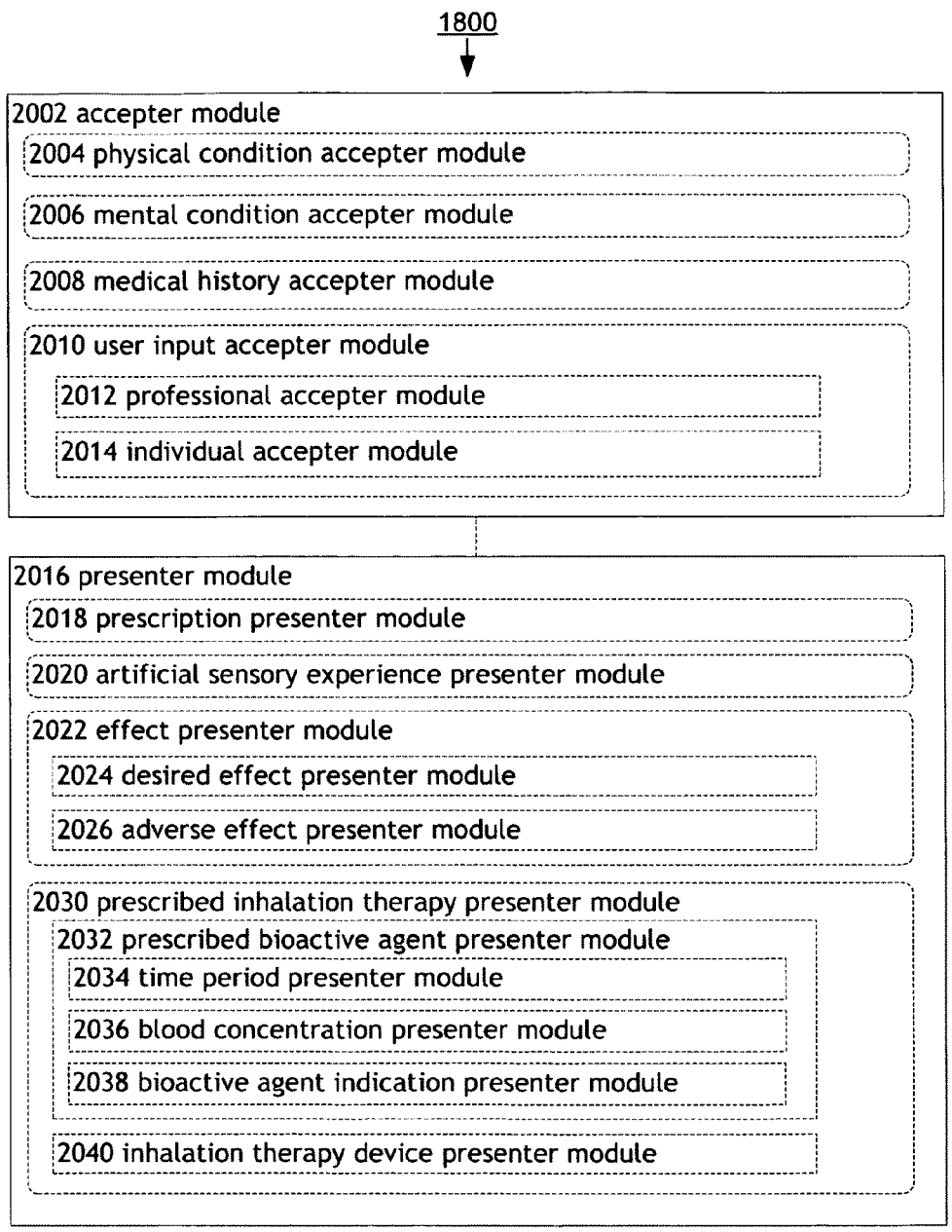
FIG. 20 illustrates an exemplary environment in which one or more technologies may be implemented.

FIG. 20 further illustrates system 1800 including accepter module 2002 and/or presenter module 2016. Accepter module 2002 may include physical condition accepter module 2004, mental condition accepter module 2006, medical history accepter module 2008, and/or user input accepter module 2010. User input accepter module 2010 may include profession accepter module 2012 and/or individual accepter module 2014. Presenter module 2016 may include prescription presenter module 2018, artificial sensory experience presenter module 2020, effect presenter module 2022, and/or prescribed inhalation therapy presenter module 2030. Effect presenter module 2022 may include desired effect presenter module 2024 and/or adverse effect presenter module 2026. Prescribed inhalation therapy presenter module 2030 may include prescribed bioactive agent presenter module 2032 and/or inhalation therapy device presenter module 2040. Prescribed bioactive agent presenter module 2032 may include time period presenter module 2034, blood concentration presenter module 2036, and/or bioactive agent indication presenter module 2038.

Figure 21:
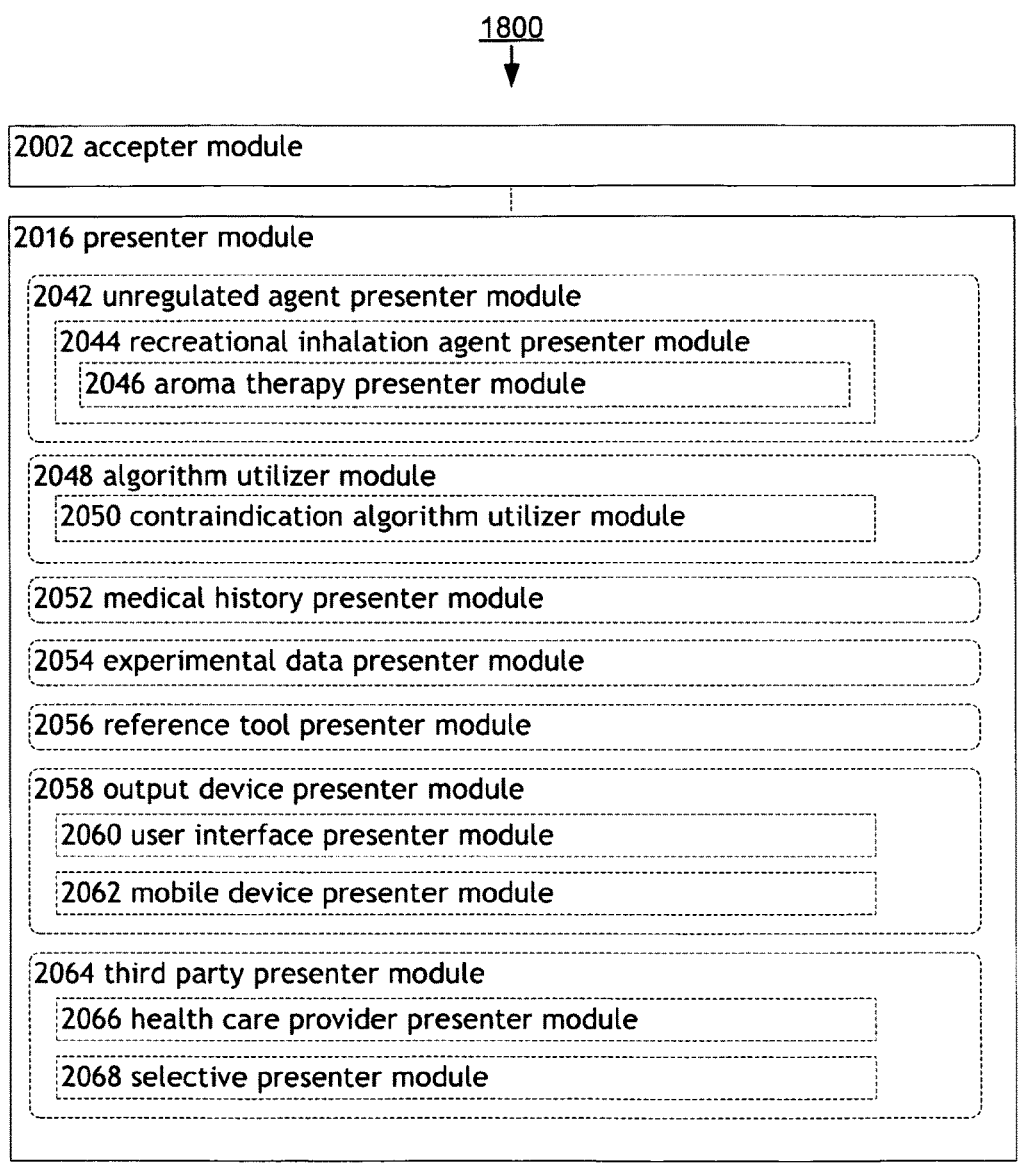
FIG. 21 illustrates an exemplary environment in which one or more technologies may be implemented.

FIG. 21 further illustrates system 1800 including accepter module 2002 and/or presenter module 2016. Presenter module 2016 may include unregulated agent presenter module 2042, algorithm utilizer module 2048, medical history presenter module 2052, experimental data presenter module 2054, reference tool presenter module 2056, output device presenter module 2058, and/or third party presenter module 2064. Unregulated agent presenter module 2042 may include recreational inhalation agent presenter module 2044. Recreational inhalation agent presenter module 2044 may include aroma therapy presenter module 2046. Algorithm utilizer module 2048 may include contraindication algorithm utilizer module 2050. Output device presenter module 2058 may include user interface presenter module 2060 and/or mobile device presenter module 2062. Third party presenter module 2064 may include health care provider presenter module 2066 and/or selective presenter module 2068.

Figure 22:
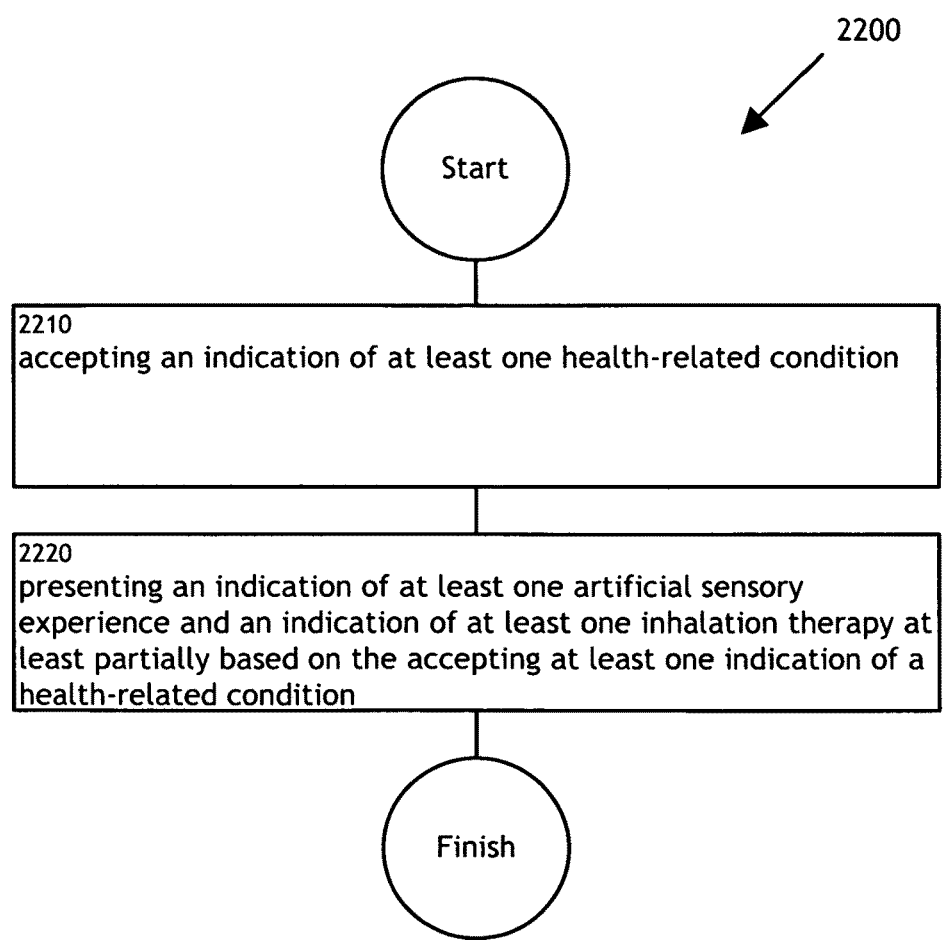
FIG. 22 illustrates an operational flow representing example operations related to combining an inhaled bioactive agent and an artificial sensory experience.

FIG. 22 illustrates an operational flow 2200 representing example operations related to accepting an indication of at least one health-related condition and presenting an indication of at least one artificial sensory experience and an indication of at least one inhalation therapy at least partially based on the accepting at least one indication of a health-related condition. In FIG. 22 and in following figures that include various examples of operational flows, discussion and explanation may be provided with respect to the above-described examples of FIGS. 18 through 21, and/or with respect to other examples and contexts. However, it should be understood that the operational flows may be executed in a number of other environments and contexts, and/or in modified versions of FIGS. 18 through 21. Also, although the various operational flows are presented in the sequence(s) illustrated, it should be understood that the various operations may be performed in other orders than those which are illustrated, or may be performed concurrently.

After a start operation, the operational flow 2200 moves to operation 2210. Operation 2210 depicts accepting an indication of at least one health-related condition. For example, as shown in FIGS. 18 through 21, accepter module 2002 may accept an indication of a health-related condition. Some examples of a health-related condition may include a physical condition, such as blood pressure and or a fever, and/or a mental condition, such as bipolar disorder and/or atypical depression. In one embodiment, accepter module 2002 may accept an indication of an anxiety disorder inputted by a psychiatrist. In some instances, accepter module 2002 may include a computer processor and/or input means, for example a keyboard, a touchscreen, a network connection, and/or a memory device.

Then, operation 2220 depicts presenting an indication of at least one artificial sensory experience and an indication of at least one inhalation therapy at least partially based on the accepting at least one indication of a health-related condition. For example, as shown in FIGS. 18 through 21, presenter module 2016 may present an indication of at least one artificial sensory experience and an indication of at least one inhalation therapy at least partially based on the accepting at least one indication of a health-related condition. One example of an artificial sensory experience may include a virtual world and/or other computer-simulated experience. Other examples of an artificial sensory experience may include experiences triggering sight, smelt, hearing, touch, and/or taste. An example of an inhalation therapy may include a bioactive agent dispensed from some device, such as a collar, bracelet, and/or necklace. In one embodiment, presenter module 2016 may present a virtual world with a mountainous environment for helping an asthma sufferer learn relaxation and a deep breathing technique. In the same embodiment, presenter module 2016 may present an inhalation therapy, such as timed dispensing of a bronchodilator, where the inhalation therapy is suitable to be combined with the virtual world. Presenting an indication of an artificial sensory experience and/or an indication of an inhalation therapy may include presenting the indication to a physician, to a computer monitor, to a mobile device, and/or to a third party. In some instances, presenter module 2016 may include a computer processor and/or a display, such as a monitor, printer, and/or a mobile device screen.

Figure 23:
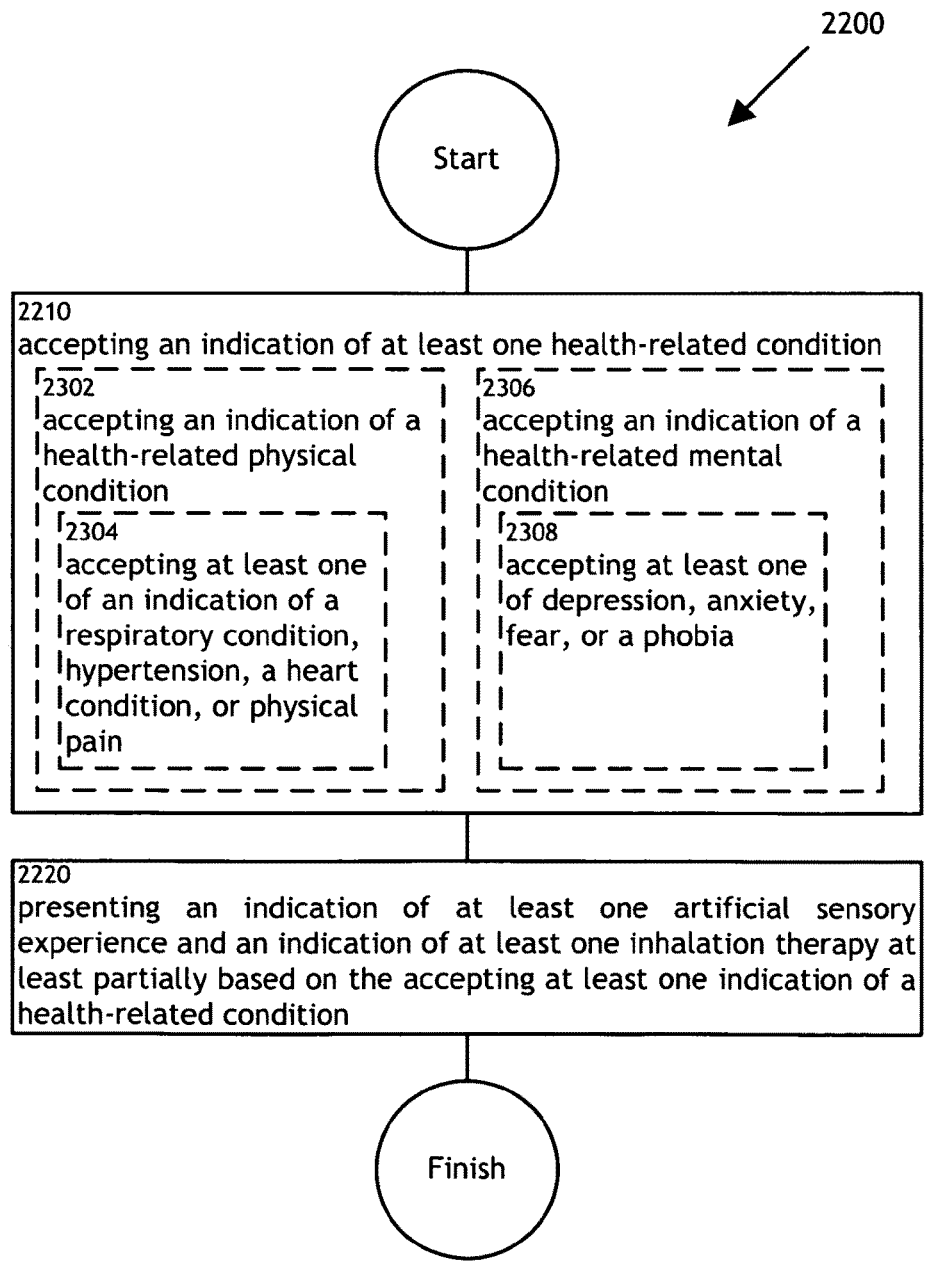
FIG. 23 illustrates an alternative embodiment of the operational flow of FIG. 22.

FIG. 23 illustrates alternative embodiments of the example operational flow 2200 of FIG. 22. FIG. 23 illustrates example embodiments where operation 2210 may include at least one additional operation. Additional operations may include operation 2302, operation 2304, operation 2306, and/or operation 2308.

Operation 2302 illustrates accepting an indication of a health-related physical condition. For example, as shown in FIGS. 18 through 21, physical condition accepter module 2004 may accept an indication of a health-related physical condition. A health-related physical condition may include the condition and/or state of the body and/or bodily function. Some examples of a health-related physical condition may include hypertension, body weight (e.g., obesity, underweight), irregular heart beat, and/or breathing irregularity (e.g., asthma). In one embodiment, physical condition accepter module 2004 may accept an indication of an individual's asthma and breathing difficulty. Another example may be found in Kurtz et al., U.S. Patent Publication No. 2008/0294012, which is incorporated herein by reference. In some instances, physical condition accepter module 2004 may a computer processor and/or input means, for example a keyboard, a touchscreen, a network connection, and/or a memory device.

Further, operation 2304 illustrates accepting at least one of an indication of a respiratory condition, hypertension, a heart condition, or physical pain. For example, as shown in FIGS. 18 through 21, physical condition accepter module 2004 may accept at least one of an indication of a respiratory condition, hypertension, a heart condition, or physical pain. A respiratory condition may include asthma, a chronic disease involving the respiratory system where airways may constrict, become inflamed, and or become lined with excessive amounts of mucus. Additional examples of a respiratory condition may include chronic obstructive pulmonary disease (COPD), emphysema, cystic fibrosis, bronchitis, chronic bronchitis, hyperresponsive airway diseases, respiratory distress syndromes (RDSs), pneumonia, and/or tuberculosis. Hypertension may include high blood pressure where blood pressure is chronically elevated. A heart condition may include any condition affecting the normal functioning of the heart, such as cardiomyopathy, cardiac arrhythmia, and/or heart failure. Physical pain may include an unpleasant awareness of a noxious stimulus and/or bodily harm. In one embodiment, physical condition accepter module 2004 may accept an indication of an individual's chronic pain inputted by the individual using a numeric pain scale, such as a numeric range from 0 to 10 points where 0 is no pain and ten is extreme pain. In some instances, physical condition accepter module 2004 may include a computer processor and/or input means, for example a keyboard, a touchscreen, a network connection, and/or a memory device.

Operation 2306 illustrates accepting an indication of a health-related mental condition. For example, as shown in FIGS. 18 through 21, mental condition accepter module 2006 may accept an indication of a health-related mental condition. A health-related mental condition may include a psychological and/or behavioral pattern in an individual and is thought to cause distress and/or disability that is not a part of normal development. Some examples of a mental condition may include dissociative disorders (depersonalization disorder and/or dissociative identity disorder), mood disorders (depression and/or bipolar disorder), anxiety disorders (obsessive-compulsive disorder and/or post-traumatic stress disorder), eating disorders, and/or personality disorders (paranoid personality disorder and/or avoidant personality disorder). In one embodiment, mental condition accepter module 2006 may accept an indication of a social phobia. In an additional embodiment, mental condition accepter module 2006 may accept an indication of atypical depression. In some instances, mental condition accepter module 2006 may include a computer processor and/or input means, for example a keyboard, a touchscreen, a network connection, and/or a memory device.

Further, operation 2308 illustrates accepting at least one of depression, anxiety, fear, or a phobia. For example, as shown in FIGS. 18 through 21, mental condition accepter module 2006 may accept at least one of depression, anxiety, fear, or a phobia. Depression may include a depressive disorder, such as atypical depression, melancholic depression, psychotic depression, and/or a depressed mood. Anxiety may include a disorder or a mood where unease, fear, and/or worry may be prevalent. Fear may include any emotional response to danger and/or threats and may include sadness and/or anger. A phobia may include a disorder and may include an irrational, persistent, and/or intense fear of certain situations, things, people, and/or activities. In one embodiment, mental condition accepter module 2006 may accept an indication of an individual's anxiety disorder. In another embodiment, mental condition accepter module 2006 may accept an indication of atypical depression. In some instances, mental condition accepter module 2006 may include a computer processor and/or input means, for example a keyboard, a touchscreen, a network connection, and/or a memory device.

Figure 24:
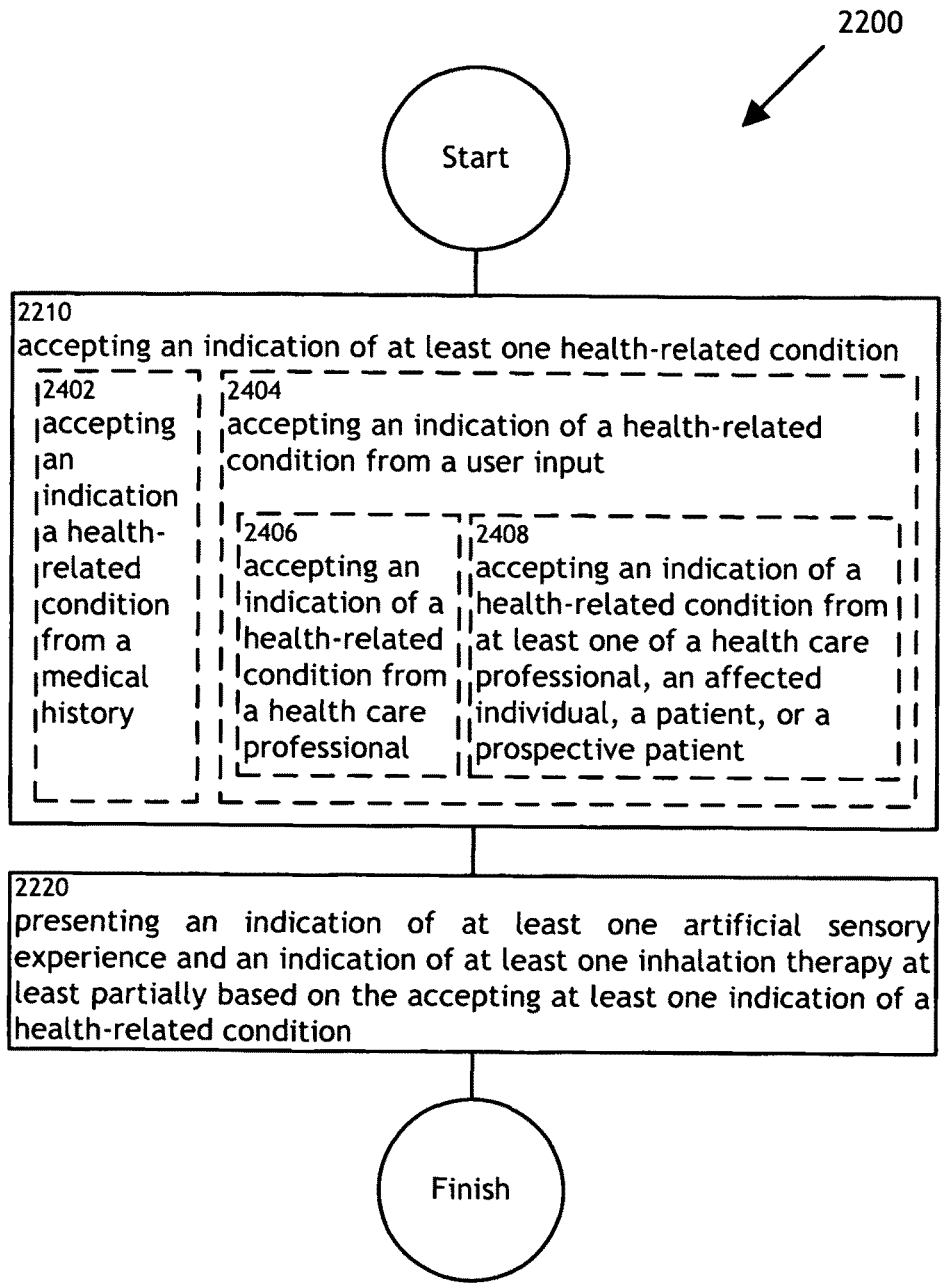
FIG. 24 illustrates an alternative embodiment of the operational flow of FIG. 22.

FIG. 24 illustrates alternative embodiments of the example operational flow 2200 of FIG. 22. FIG. 24 illustrates example embodiments where operation 2210 may include at least one additional operation. Additional operations may include operation 2402, operation 2404, operation 2406, and/or operation 2408.

Operation 2402 illustrates accepting an indication a health-related condition from a medical history. For example, as shown in FIGS. 18 through 21, medical history accepter module 2008 may accept an indication of a health-related condition from a medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history accepter module 2008 may accept an indication of a record of an individual's past treatment, which may indicate a likelihood of potential combination artificial sensory experience and inhalation therapy efficacy. In this embodiment, the personal medical history may indicate that an individual may be averse to a certain virtual world, such as a virtual world with rapid animation that may cause nausea, or averse to a specific inhaled bioactive agent. In some instances, medical history accepter module 2008 may include a computer processor and/or input means, for example a keyboard, a touchscreen, a network connection, and/or a memory device.

Operation 2404 illustrates accepting an indication of a health-related condition from a user input. For example, as shown in FIGS. 18 through 21, user input accepter module 2010 may accept an indication of a health-related condition from a user input. In one embodiment, user input accepter module 2010 may accept an indication of a health-related condition from a touchscreen. A user input may include any device used to input information. One example of a user input may include a peripheral computer device, such as a scanner, a microphone, a RAM drive, a keyboard, and/or a barcode reader. In some instances, user input accepter module 2010 may include a computer processor and/or input means, for example a keyboard, a touchscreen, a network connection, and/or a memory device.

Further, operation 2406 illustrates accepting an indication of a health-related condition from a health care professional. For example, as shown in FIGS. 18 through 21, professional accepter module 2012 may accept an indication of a health-related condition from a health care professional. A health care professional may include a physician, a mental health specialist, a nurse, a physical therapist, an occupational therapist, a chiropractor, and/or a homeopathic practitioner. In one embodiment, professional accepter module 2012 may accept an indication of hypertension from a physician. In another embodiment, professional accepter module 2012 may accept an indication of atypical depression from a psychiatrist. In some instances, professional accepter module 2012 may include a computer processor and/or input means, for example a keyboard, a touchscreen, a network connection, and/or a memory device.

Further, operation 2408 illustrates accepting an indication of a health-related condition from at least one of an affected individual, a patient, or a prospective patient. For example, as shown in FIGS. 18 through 21, individual accepter module 2014 may accept an indication of a health-related condition from at least one of an affected individual, a patient, or a prospective patient. In one embodiment, individual accepter module 2014 may accept an indication of a health-related condition from a prospective patient. In this embodiment, the prospective patient may be investigating whether a certain therapy may be appropriate and/or effective for the prospective patient. By entering a health related condition, an affected individual, a patient, or a prospective patient may be able to determine a more accurately tailored therapy. In another embodiment, individual accepter module 2014 may accept an indication of a health-related condition from a patient. In this embodiment, the patient may have experienced a portion of a combination artificial sensory experience and an inhaled bioactive agent therapy session and the individual accepter module 2014 may accept an indication of a health-related condition for the purpose of reevaluating the effectiveness of the artificial sensory experience and/or the inhaled bioactive agent. In some instances, individual accepter module 2014 may include a computer processor and/or input means, for example a keyboard, a touchscreen, a network connection, and/or a memory device.

Figure 25:
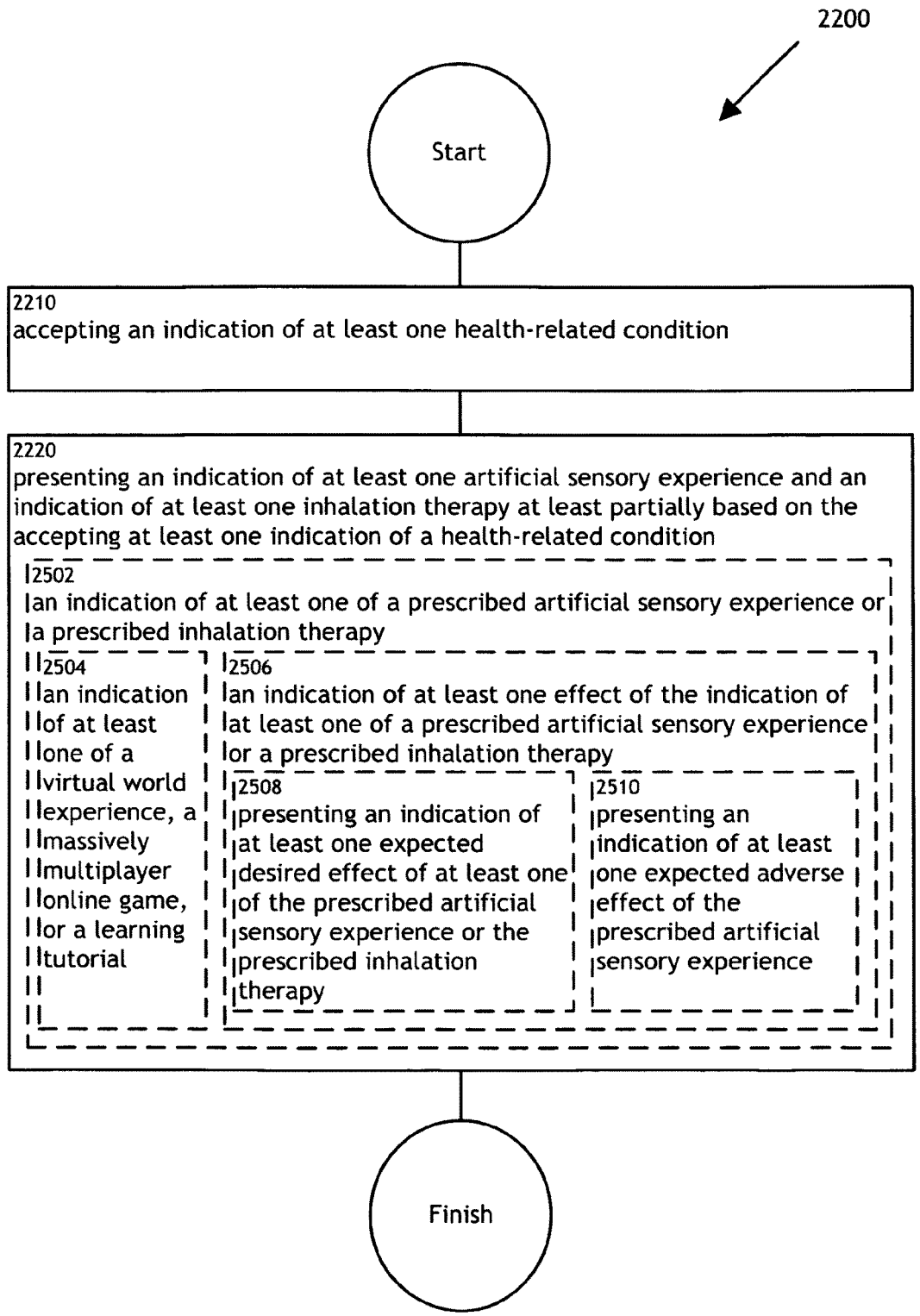
FIG. 25 illustrates an alternative embodiment of the operational flow of FIG. 22.

FIG. 25 illustrates alternative embodiments of the example operational flow 2200 of FIG. 22. FIG. 25 illustrates example embodiments where operation 2220 may include at least one additional operation. Additional operations may include operation 2502, operation 2504, operation 2506, operation 2508, and/or operation 2510.

Operation 2502 illustrates an indication of at least one of a prescribed artificial sensory experience or a prescribed inhalation therapy. For example, as shown in FIGS. 18 through 21, prescription presenter module 2018 may present an indication of a prescribed artificial sensory experience or a prescribed inhalation therapy. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription presenter module 2018 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. A prescribed inhalation therapy may include an inhalation therapy prescribed by a health care professional, such as a physician, a mental health specialist, a nurse, a physical therapist, an occupational therapist, a chiropractor, and/or a homeopathic practitioner. Some examples of a prescribed inhalation therapy may include prescribing an inhaled corticosteroid to an asthma sufferer and/or prescribing inhaled insulin, such as Exubera, manufactured by Pfizer, to an individual with diabetes. In some instances, prescription presenter module 2018 may include a computer processor and/or a display device, such as a computer monitor and/or a printer.

Further, operation 2504 illustrates an indication of at least one of a virtual world experience, a massively multiplayer online game, or a learning tutorial. For example, as shown in FIGS. 18 through 21, artificial sensory experience presenter module 2020 may present an indication of a virtual world experience, a massively multiplayer online game, or a learning tutorial. A virtual world experience may include a computer-based simulated environment intended to be interactive. Some examples of a virtual world experience may include a text-based chat room, computer conferencing, an online game, a single player game, and/or a computer tutorial. A massively multiplayer online game may include a video game capable of supporting multiple players, such as World of Warcraft and/or SecondLife. An online learning tutorial may include a screen recording, a written document (either online or downloadable), or an audio file, where a user may be given step by step instructions on how to do something. In one embodiment, artificial sensory experience presenter module 2020 may present an indication of a virtual world experience, such as World of Warcraft. In some instances, artificial sensory experience presenter module 2020 may include a computer processor.

Further, operation 2506 illustrates an indication of at least one effect of the indication of at least one of a prescribed artificial sensory experience or a prescribed inhalation therapy. For example, as shown in FIGS. 18 through 21, effect presenter module 2022 may present an indication of at least one effect of the indication of at least one of a prescribed artificial sensory experience or a prescribed inhalation therapy. In one embodiment, effect presenter module 2022 may present an indication of at least one effect of the prescribed artificial sensory experience, such as an increased breathing capacity in an individual where an inhaled steroid has been administered. An effect may include a reaction and/or thing that occurs as a result of the artificial sensory experience. For example, an effect may include a side effect, a desired effect, and/or an adverse effect. Some examples of an effect may include an altered bioactive agent efficacy, dizziness, and/or a decreased heart rate. In some instances, effect presenter module 2022 may include a computer processor.

Further, operation 2508 illustrates presenting an indication of at least one expected desired effect of at least one of the prescribed artificial sensory experience or the prescribed inhalation therapy. For example, as shown in FIGS. 18 through 21, desired effect presenter module 2024 may present an indication of at least one desired effect of the prescribed artificial sensory experience. Some examples of a desired effect may include effects such as an increased bioactive agent efficacy, a cured illness and/or condition, and/or a changed behavior. In one embodiment, desired effect presenter module 2024 may present an indication of an increased steroid efficacy measured by measuring an individual's breathing capacity. In some embodiments, desired effect presenter module 2024 may present an indication of an expected change in a desired effect of a bioactive agent administered via an inhalation device. Such an expected change may include subjective measures such as better breathing, reduced pain, and/or better mood. Alternatively or in addition, such an expected change may involve objective measures such as lower blood pressure, lower pulse, decreased frequency of nervous body movement, or the like. Such objective measures may be detected by, for example, inhalation device 110 and/or virtual reality headset 114. Such a change in a desired effect may be associated with administration of an artificial sensory experience together with a bioactive agent via an inhalation device. In some instances, desired effect presenter module 2024 may include a computer processor and/or a display, such as a monitor and/or a printer.

Further, operation 2510 illustrates presenting an indication of at least one expected adverse effect of the prescribed artificial sensory experience. For example, as shown in FIGS. 18 through 21, adverse effect presenter module 2026 may present an indication of an expected adverse effect of a prescribed artificial sensory experience. An adverse effect may include a harmful and/or undesired effect resulting from an intervention, such as a prescribed artificial sensory experience. Some examples of an adverse effect may include headache, dizziness, depression, bleeding, seizure, and/or fever. In one embodiment, adverse effect presenter module 2026 may present an indication of fever in an individual while being administered a prescribed artificial sensory experience and an inhaled bioactive agent. In some embodiments, adverse effect presenter module 2026 may present an indication of an expected change in a side effect of a bioactive agent administered via an inhalation device. Such an expected change may include reduced fever, reduced pain, and/or reduced frequency of a side effect. Such a change in a side effect may be associated with administration of an artificial sensory experience together with a bioactive agent via an inhalation device. In some embodiments, a change in adverse effect may be detected by an inhalation device and/or artificial sensory experience. In some instances, adverse effect presenter module 2026 may include a computer processor, a display device, such as a monitor and/or printer, and/or medical instrumentation, such as a thermometer configured for measuring a body temperature.

Figure 26:
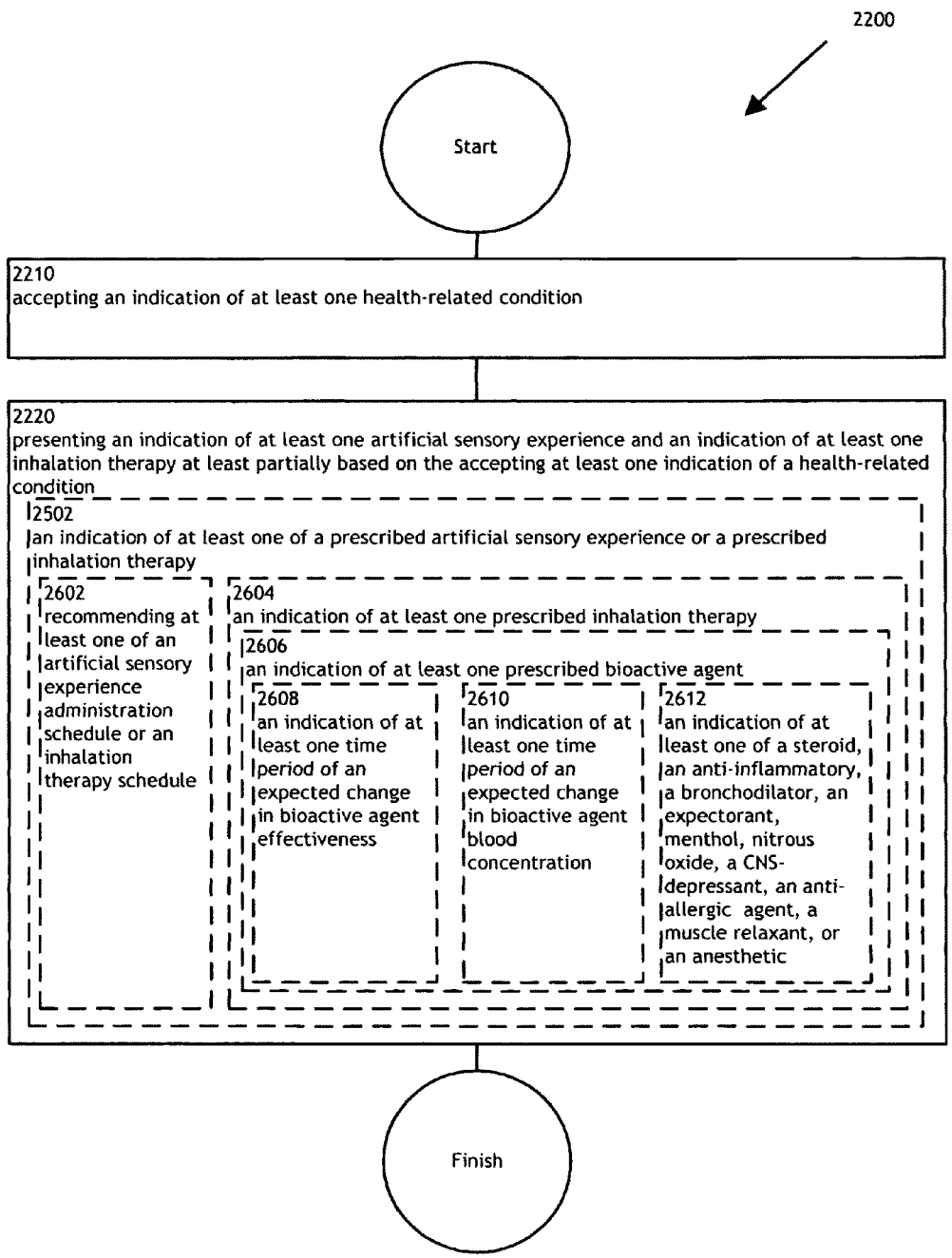
FIG. 26 illustrates an alternative embodiment of the operational flow of FIG. 22.

FIG. 26 illustrates alternative embodiments of the example operational flow 2200 of FIG. 22. FIG. 26 illustrates example embodiments where operation 2220 may include at least one additional operation. Additional operations may include operation 2602, operation 2604, operation 2606, operation 2608, operation 2610, and/or operation 2612.

Further, operation 2602 illustrates recommending at least one of an artificial sensory experience administration schedule or an inhalation therapy schedule. For example, as shown in FIGS. 18 through 21, recommender module 2028 may recommend an artificial sensory experience administration schedule or an inhalation therapy schedule. In one embodiment, recommender module 2028 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In an additional embodiment, recommender module 2028 may recommend a schedule for administration of an inhaled corticosteroid. In some instances, recommender module 2028 may include a computer processor.

Operation 2604 illustrates an indication of at least one prescribed inhalation therapy. For example, as shown in FIGS. 18 through 21, prescribed inhalation therapy presenter module 2030 may present an indication of at least one prescribed inhalation therapy. In one embodiment, prescribed inhalation therapy presenter module 2030 may present an indication of aerially diffused salmeterol prescribed by a physician. Some other examples of a prescribed inhalation therapy may include steroids, bronchodilators, anesthetics, insulin, flu vaccine, and/or inhaled anticholinergics. In some instances, prescribed inhalation therapy presenter module 2030 may include a computer processor, a display, and/or a printer.

Further, operation 2606 illustrates an indication of at least one prescribed bioactive agent. For example, as shown in FIGS. 18 through 21, prescribed bioactive agent presenter module 2032 may present an indication of at least one prescribed bioactive agent. A prescribed bioactive agent may include any bioactive agent prescribed by a health care professional, such as a physician, a mental health specialist, a nurse, a physical therapist, an occupational therapist, a chiropractor, and/or a homeopathic practitioner. In one embodiment, prescribed bioactive agent presenter module 2032 may present an indication of a prescribed combination of fluticasone and salmeterol suitable for use with an artificial sensory experience. In this embodiment, the combined prescribed bioactive agent and artificial sensory experience may serve to manage an individual's asthma and chronic obstructive pulmonary disease (COPD). In some instances, prescribed bioactive agent presenter module 2032 may include a computer processor, a display, and/or a printer.

Further, operation 2608 illustrates an indication of at least one time period of an expected change in bioactive agent effectiveness. For example, as shown in FIGS. 18 through 21, time period presenter module 2034 may present an indication of at least one time period of an expected change in bioactive agent effectiveness. In one embodiment, time period presenter module 2034 may present an indication of a time period when a bronchodilator is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, time period presenter module 2034 may present an indication of a time period where a steroid concentration in an individual's blood stream drops. This time period of low blood stream steroid concentration may be appropriate for presenting an immersive virtual world for serving as compensation for a possible lack of steroid effectiveness caused by lowered steroid blood concentration. In some instances, time period presenter module 2034 may include a computer processor.

Further, operation 2610 illustrates an indication of at least one time period of an expected change in bioactive agent blood concentration. For example, as shown in FIGS. 18 through 21, blood concentration presenter module 2036 may present an indication of at least one time period of an expected change in bioactive agent blood concentration. In one embodiment, blood concentration presenter module 2036 may present an indication of a one hour time period of an expected change in steroid blood concentration. Indicating a time period showing a change in blood concentration may serve to help determine an artificial sensory experience administration schedule and/or a bioactive agent inhalation schedule. For example, if a bioactive agent blood concentration is expected to be reduced during a certain time period, an artificial sensory experience configured for distracting an individual from pain may be selected for administration during that time period. Additionally, an inhaled bioactive agent may be complimented with a separate bioactive agent for compensating for reduced effectiveness and/or a synergistic effect. Further, bioactive agent blood concentration may include bioavailability of the agent. In some instances, blood concentration presenter module 2036 may include a computer processor and/or a display device, such as a printer and/or a computer monitor.

Further, operation 2612 illustrates an indication of at least one of a steroid, an anti-inflammatory, a bronchodilator, an expectorant, menthol, nitrous oxide, a CNS-depressant, an anti-allergic agent, a muscle relaxant, or an anesthetic. For example, as shown in FIGS. 18 through 21, bioactive agent indication presenter module 2038 may present an indication of at least one of a steroid, an anti-inflammatory, a bronchodilator, an expectorant, menthol, nitrous oxide, a CNS-depressant, an anti-allergenic agent, a muscle relaxant, or an anesthetic. One example of a steroid may include an anabolic steroid, which may be a derivative of androgens (such as testosterone), for stimulating growth. Another example of a steroid may include a corticosteroid, which may be often used as an anti-inflammatory prescribed for asthma. An anti-inflammatory may include a bioactive agent utilized to treat and/or reduce inflammation. Some examples of an anti-inflammatory may include glucocorticoids, ibuprofen, and/or naproxen. A bronchodilator may include a substance that dilates the bronchi and bronchioles decreasing airway resistance and thereby facilitating airflow. An expectorant may include a bioactive agent used for dissolving and/or bringing up mucus from the lungs, respiratory tract, and/or trachea. Some examples of an expectorant may include guaifenesin and/or tyloxapol. Menthol may include an organic and/or synthetic compound with local anesthetic and counterirritant qualities often used for relieving throat irritation and/or as a decongestant. Nitrous oxide may include a gas often used as a weak general anesthetic. A CNS-depressant, such as benzodiazepine and/or a sedative, may include a class of psychoactive drugs with varying hypnotic, sedative, anxiolytic, anticonvulsant, muscle relaxant and amnesic properties, which may be mediated by slowing down the central nervous system. In one embodiment, bioactive agent indication presenter module 2038 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function and/or decreasing muscle tone. One example of a muscle relaxant may include a methylxanthine, such as Theophylline. Another example of a muscle relaxant may include an anti-spasmodic (dicyclomine, hyoscyamine, and/or peppermint oil). An anesthetic may include an inhalational general anesthetic, such as halothane, desflurane, enflurane, isoflurane, and/or sevoflurane. In some instances, bioactive agent indication presenter module 2038 may include a computer processor, a printer, a display, and/or a mobile device.

Figure 27:
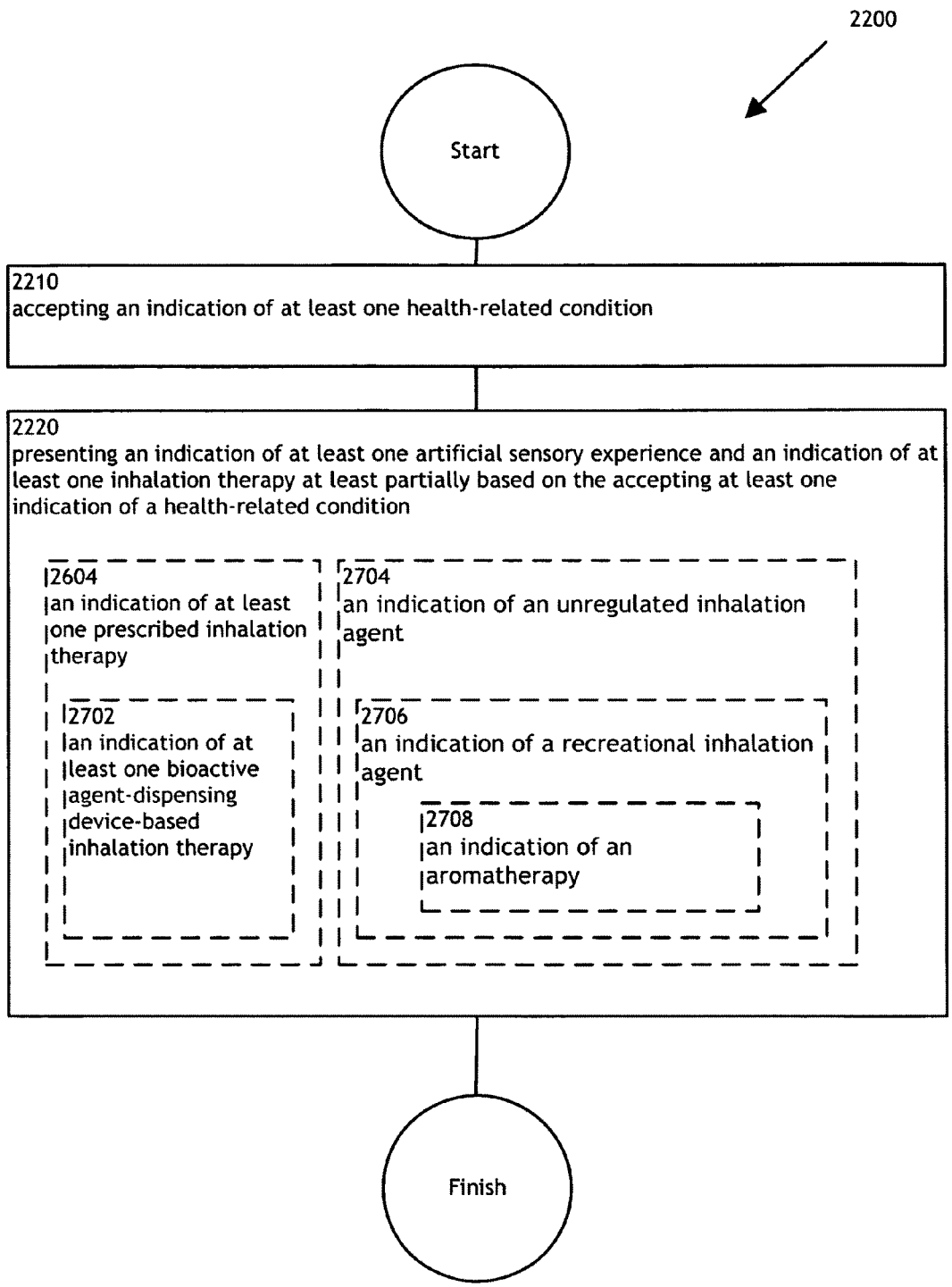
FIG. 27 illustrates an alternative embodiment of the operational flow of FIG. 22.

FIG. 27 illustrates alternative embodiments of the example operational flow 2200 of FIG. 22. FIG. 27 illustrates example embodiments where operation 2220 may include at least one additional operation. Additional operations may include operation 2702, operation 2704, operation 2706, and/or operation 2708.

Further, operation 2702 illustrates an indication of at least one bioactive agent-dispensing device-based inhalation therapy. For example, as shown in FIGS. 18 through 21, inhalation therapy device presenter module 2040 may present an indication of a bioactive agent-dispensing device-based inhalation therapy. In one embodiment, inhalation therapy device presenter module 2040 may present an indication of a therapy using a headset utilizing an albuterol dispenser for use with an artificial sensory experience. In this embodiment, an artificial sensory experience may serve to assist an asthma sufferer in learning deep breathing and relaxation techniques. Other devices suitable with an inhalation therapy may include a bioactive agent-dispensing collar, a bioactive agent-dispensing necklace, and/or a bioactive agent-dispensing bracelet. In some instances, inhalation therapy device presenter module 2040 may include a computer processor, a printer, a display, and/or a mobile device.

Operation 2704 illustrates an indication of an unregulated inhalation agent. For example, as shown in FIGS. 18 through 21, unregulated agent presenter module 2042 may present an indication of an unregulated inhalation agent. An unregulated inhalation agent may include an agent that is not regulated by law and/or may be available without a medical prescription. Some examples of an unregulated inhalation agent may include an aromatherapeutic, smoke, menthol, and/or an enriched oxygen mixture. In one embodiment, unregulated agent presenter module 2042 may present an indication of an enriched oxygen mixture, which is often used as a mild euphoric and/or a performance booster, for an individual's use during an exercise session while experiencing a virtual world, e.g., while playing Wii fit. In some instances, unregulated agent presenter module 2042 may include a computer processor, a computer display, and/or a computer printer.

Further, operation 2706 illustrates an indication of a recreational inhalation agent. For example, as shown in FIGS. 18 through 21, recreational inhalation agent presenter module 2044 may present an indication of a recreation inhalation agent. In one embodiment, recreational inhalation agent presenter module 2044 may present an indication of an aromatherapeutic. Some other examples of a recreational inhalation agent may include smoke (for example, simulating proximity to a campfire) and/or a scent (for example, use in a virtual scent environment, such as a learning environment, e.g., cooking and/or chemistry). Another example of a recreational inhalation agent may include an inhalation agent for a ceremonial purpose, such as tobacco smoke. In some instances, recreational inhalation agent presenter module 2044 may include a computer processor, a computer display, and/or a printer.

Further, operation 2708 illustrates an indication of an aromatherapy. For example, as shown in FIGS. 18 through 21, aroma therapy presenter module 2046 may present an indication of an aroma therapy. Aromatherapy may include the use of an aromatherapeutic, which may include a volatile material, such as an essential oil. Some examples of an aromatherapeutic may include essential oils (eucalyptus oil and/or grapefruit oil), absolutes (jasmine and/or rose absolute), herbal distillates (lemon balm and/or chamomile), and/or a volatile medication, such as a decongestant with menthol. The volatile material may be applied using aerial diffusion, direct inhalation, and/or a topical application. In one embodiment, aroma therapy presenter module 2046 may present an indication of aerial diffusion of chamomile, which may often be used to overcome anxiety and/or depression. In this embodiment, the aerial diffusion of chamomile may be tailored to be coupled with an artificial sensory experience, such as a calming virtual world, where the individual experiencing the therapy may experience a calming environment. An additional example of a diffused aromatherapy may be found in Jendrucko et al., U.S. Pat. No. 7,427,417, which is incorporated herein by reference. In some instances, aroma therapy presenter module 2046 may include a computer processor, a printer, and/or a computer display.

Figure 28:
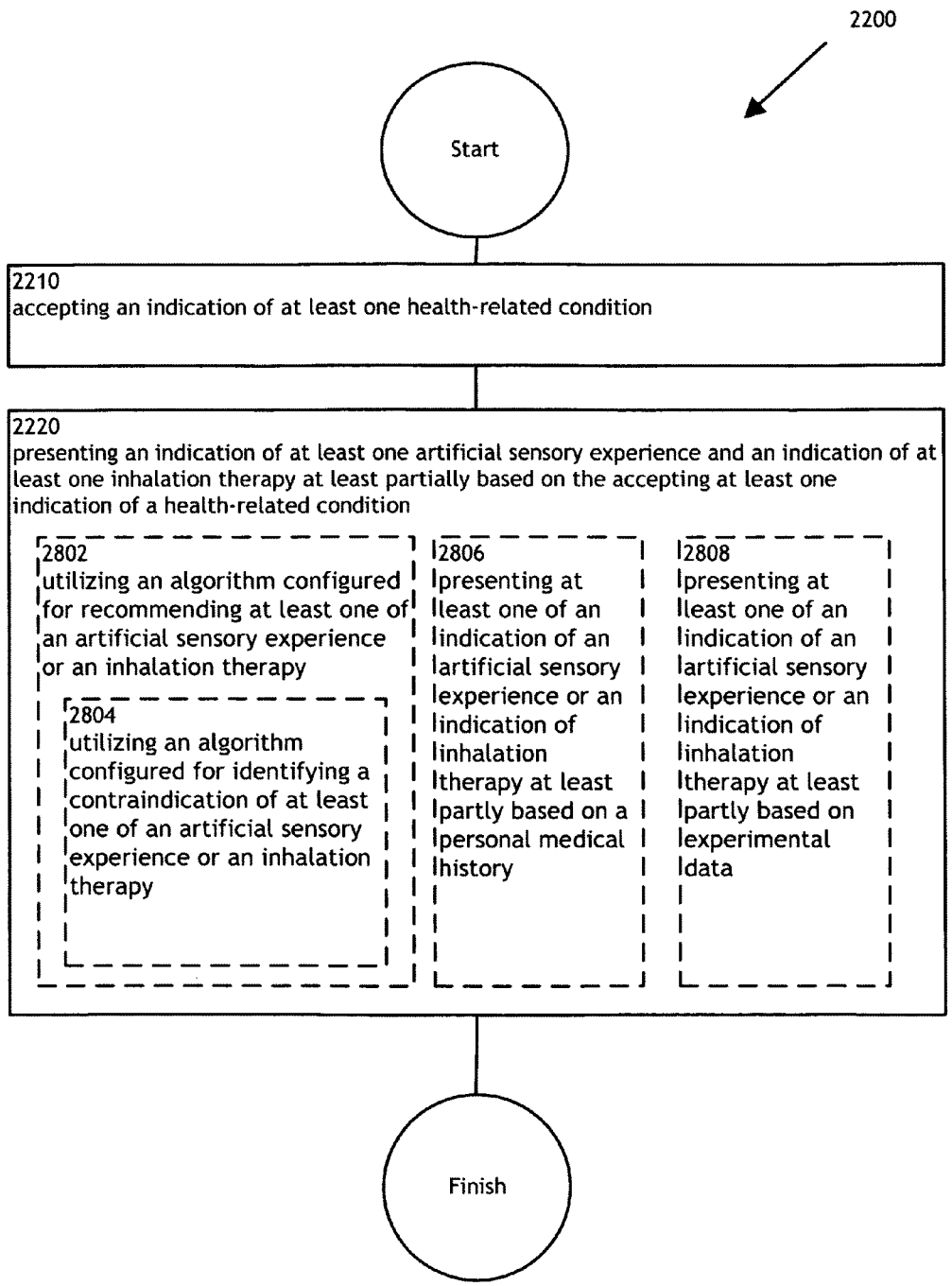
FIG. 28 illustrates an alternative embodiment of the operational flow of FIG. 22.

FIG. 28 illustrates alternative embodiments of the example operational flow 2200 of FIG. 22. FIG. 28 illustrates example embodiments where operation 2220 may include at least one additional operation. Additional operations may include operation 2802, operation 2804, operation 2806, and/or operation 2808.

Operation 2802 illustrates utilizing an algorithm configured for recommending at least one of an artificial sensory experience or an inhalation therapy. For example, as shown in FIGS. 18 through 21, algorithm utilizer module 2048 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 2048 may utilize an algorithm that uses an inputted indication of an analgesic, such as oxycodone, and determines a suitable artificial sensory experience by analyzing periods of low blood concentration of the oxycodone. In this embodiment, algorithm utilizer module 2048 may recommend an artificial sensory experience that may be effective in pain distraction when bioactive agent blood concentration may be reduced but before an additional dose may be available. In an additional embodiment, algorithm utilizer module 2048 may recommend an inhalation therapy suitable to be used with a specified artificial sensory experience, such as a virtual world, by using an inputted artificial sensory experience and determining the inhalation therapy. In this embodiment, determining the inhalation therapy may include using a database, comparing compatibility between an artificial sensory experience and an inhalation therapy, clinical trials, and/or considering a medical history. In some instances, algorithm utilizer module 2048 may include a computer processor.

Further, operation 2804 illustrates utilizing an algorithm configured for identifying a contraindication of at least one of an artificial sensory experience or an inhalation therapy. For example, as shown in FIGS. 18 through 21, contraindication algorithm utilizer module 2050 may utilize an algorithm configured for identifying a contraindication of the artificial sensory experience. A contraindication of an artificial sensory experience may include giving an indication against the advisability of the artificial sensory experience. For example, contraindication algorithm utilizer module 2050 may utilize an algorithm that considers an individual's personal medical history, such as a phobia, and may recommend not prescribing a certain artificial sensory experience, which may include an object that may trigger the phobia. Contraindication algorithm utilizer module 2050 may identify a contraindication of an artificial sensory experience for reasons such as an adverse effect and/or inefficacy. In some instances, contraindication algorithm utilizer module 2050 may include a computer processor.

Operation 2806 illustrates presenting at least one of an indication of an artificial sensory experience or an indication of inhalation therapy at least partly based on a personal medical history. For example, as shown in FIGS. 18 through 21, medical history presenter module 2052 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history presenter module 2052 may present an indication of a suitable virtual world based on a personal medical history. In this embodiment, the personal medical history may indicate that an individual may be averse to a certain virtual world, such as a virtual world with rapid animation that may cause nausea. In another embodiment, medical history presenter module 2052 may present an indication of a suitable inhalation therapy based on a personal medical history indicating that an individual may favorably respond to the inhalation therapy, such as a collar-dispensed bronchodilator. In some instances, medical history presenter module 2052 may include a computer processor and/or a display device, such as a computer monitor and/or a printer.

Operation 2808 illustrates presenting at least one of an indication of an artificial sensory experience or an indication of inhalation therapy at least partly based on experimental data. For example, as shown in FIGS. 18 through 21, experimental data presenter module 2054 may present an indication of an artificial sensory experience at least partly based on experimental data. Experimental data may include any data from an experiment, such as a clinical trial. The experiment may be an experiment including an individual and/or a group of people. In one embodiment, experimental data presenter module 2054 may present an indication of a virtual world suitable for an individual based on a clinical trial involving a group of 1,000 people showing a certain success rate for reducing a phobia, such as fear of heights. In an additional embodiment, experimental data presenter module 2054 may present an indication of an inhalation therapy tailored to an individual's needs based on a clinical trial involving a group of 500 people showing a certain success rate for learning a more efficient breathing technique. In some instances, experimental data presenter module 2054 may include a computer processor and/or a display device, such as a computer monitor, a mobile phone, and/or a printer.

Figure 29:
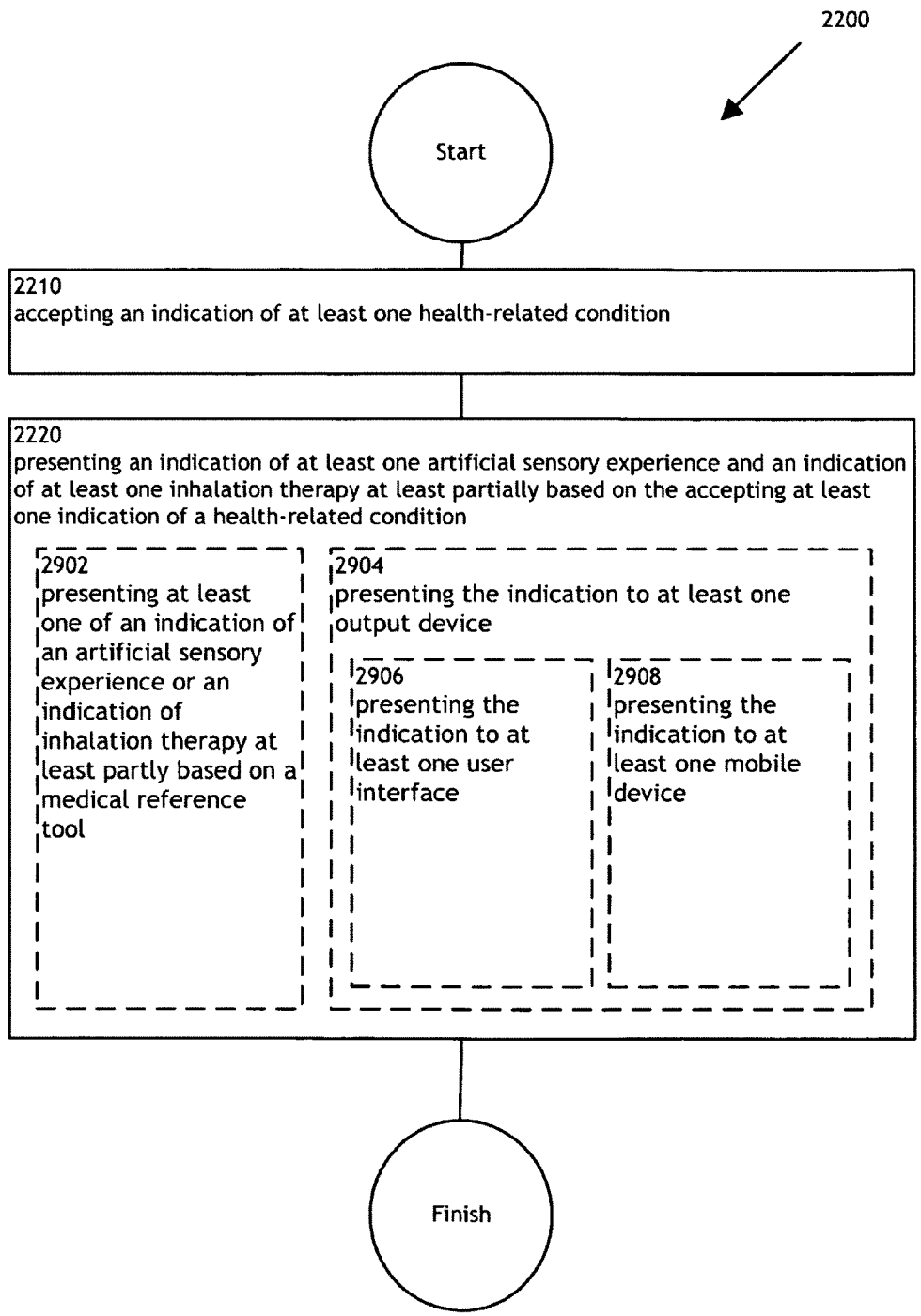
FIG. 29 illustrates an alternative embodiment of the operational flow of FIG. 22.

FIG. 29 illustrates alternative embodiments of the example operational flow 2200 of FIG. 22. FIG. 29 illustrates example embodiments where operation 2220 may include at least one additional operation. Additional operations may include operation 2902, operation 2904, operation 2906, and/or operation 2908.

Operation 2902 illustrates presenting at least one of an indication of an artificial sensory experience or an indication of inhalation therapy at least partly based on a medical reference tool. For example, as shown in FIGS. 18 through 21, reference tool presenter module 2056 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, reference tool presenter module 2056 may present an indication of an artificial sensory experience based on a reference database, such as a database including data from a clinical trial. In an additional embodiment, reference tool presenter module 2056 may present an indication of an inhalation therapy, such as albuterol released from a collar, where the inhalation therapy is listed in a drug and artificial sensory experience interaction database. In some instances, reference tool presenter module 2056 may include a computer processor and/or a display device, such as a mobile phone, a printer, and/or a computer monitor.

Operation 2904 illustrates presenting the indication to at least one output device. For example, as shown in FIGS. 18 through 21, output device presenter module 2058 may present to at least one output device. In one example, output device presenter module 2058 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134 and/or user 118. In some instances, output device presenter module 2058 may include a computer processor.

Further, operation 2906 illustrates presenting the indication to at least one user interface. For example, as shown in FIGS. 18 through 21, user interface presenter module 2060 may present to at least one user interface. In one embodiment, user interface presenter module 2060 may present to a touchscreen device. A user interface may include means by which an individual may interact with a system. Some examples of a user interface may include a touchscreen, a graphical user interface, a tactile interface, and/or a live user interface. In some instances, user interface presenter module 2060 may include a computer processor.

Further, operation 2908 illustrates presenting the indication to at least one mobile device. For example, as shown in FIGS. 18 through 21, mobile device presenter module 2062 may present to at least one mobile device. In one embodiment, mobile device presenter module 2062 may present to a mobile phone. A mobile device may include a portable computing device and may have wireless connection capability. Some examples of a mobile device may include a laptop or notebook computer, a personal digital assistant (PDA), an iPod, a smartphone, an Enterprise digital assistant (EDA), and/or a pager. In some instances, mobile device presenter module 2062 may include a computer processor.

Figure 30:
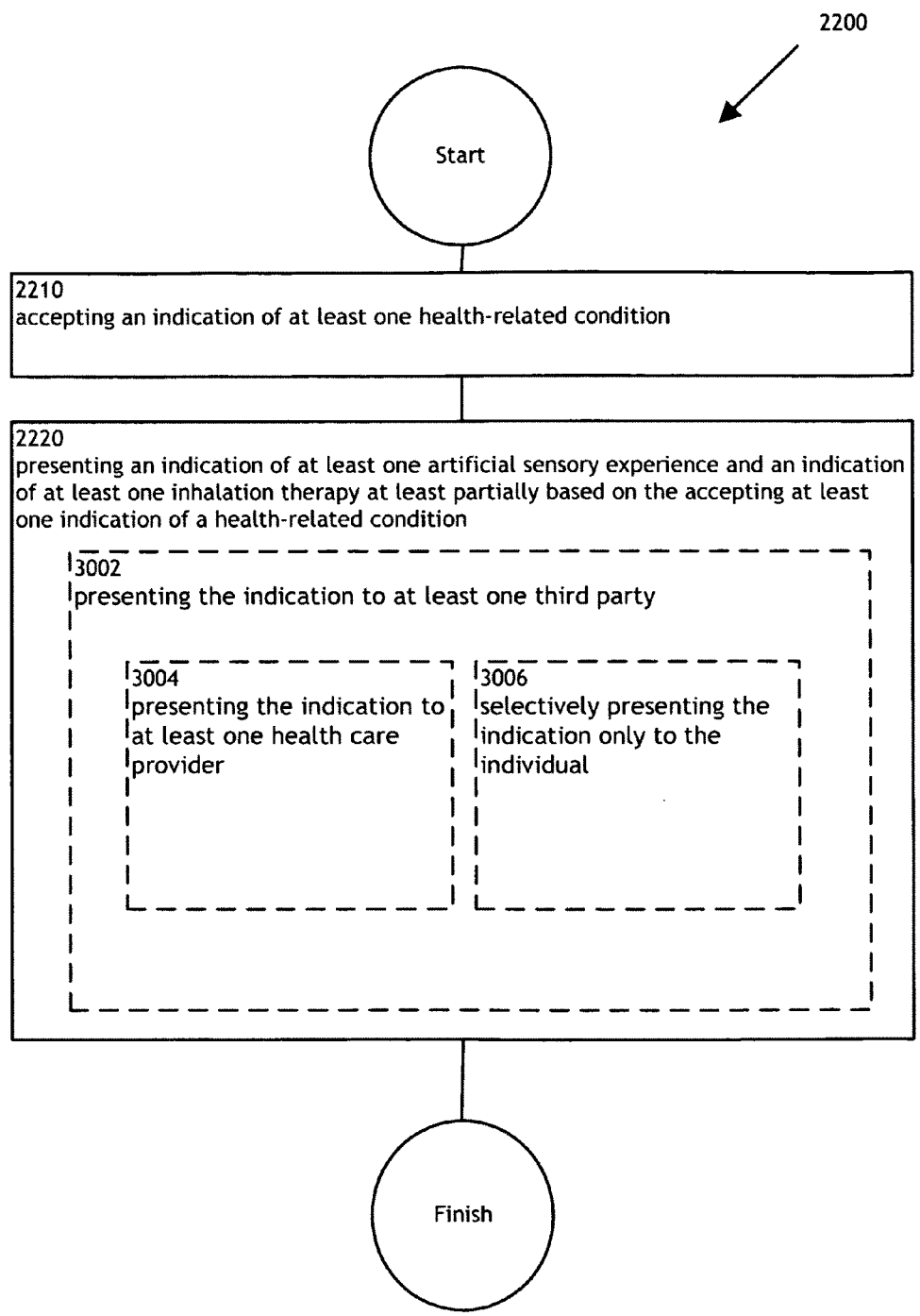
FIG. 30 illustrates an alternative embodiment of the operational flow of FIG. 22.

FIG. 30 illustrates alternative embodiments of the example operational flow 2200 of FIG. 22. FIG. 30 illustrates example embodiments where operation 2220 may include at least one additional operation. Additional operations may include operation 3002, operation 3004, and/or operation 3006.

Operation 3002 illustrates presenting the indication to at least one third party. For example, as shown in FIGS. 18 through 21, third party presenter module 2064 may present to an individual's physician. A third party may include a party that is an independent party, person, and/or entity. Some examples of a third party may include a physician, a medical database, a hospital, a law enforcement agency, and/or a pharmacy. In one embodiment, third party presenter module 2064 may present an indication to an insurance company. Another example of reporting to a third party may include creating displays and reports for aggregating data from therapy results, further discussed in Bair et al., U.S. Pat. No. 6,067,523, which is incorporated herein by reference. In some instances, third party presenter module 2064 may include a computer processor and/or a communications device, such as a monitor and network link.

Further, operation 3004 illustrates presenting the indication to at least one health care provider. For example, as shown in FIGS. 18 through 21, health care provider presenter module 2066 may present to a health care provider. A health care provider may include a pharmacy, a pharmaceutical company, a medical device company, a research institution, a computer software and/or computer hardware company, a website, a nurse and/or a physician. In one embodiment, health care provider presenter module 2066 may present to a physician a prescribed combination artificial sensory experience and bioactive agent therapy via a secured website. In some instances, health care provider presenter module 2066 may include a computer processor.

Further, operation 3006 illustrates selectively presenting the indication only to the individual. For example, as shown in FIGS. 18 through 21, selective presenter module 2068 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 2068 may present only to individual 134 and may keep results of a certain combination therapy confidential. In one embodiment, an encryption key may be employed to protect selected information. In an additional example, selective presenter module 2068 may report only to a law enforcement agency and/or representative, such as a probation officer, and not to individual 134. In some instances, selective presenter module 2068 may include a computer processor.

Figure 31:
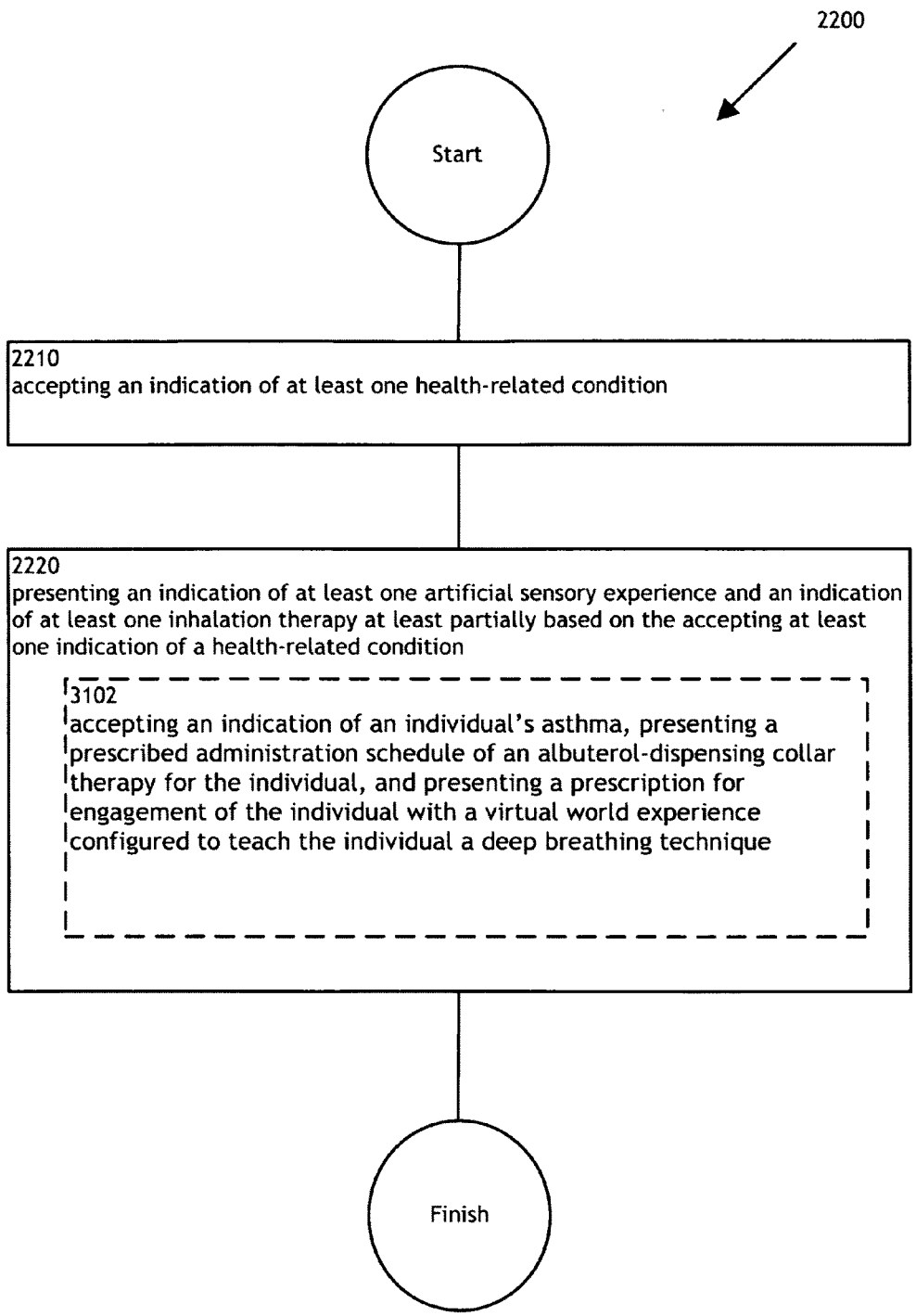
FIG. 31 illustrates an alternative embodiment of the operational flow of FIG. 22.

FIG. 31 illustrates alternative embodiments of the example operational flow 2200 of FIG. 22. FIG. 31 illustrates example embodiments where operation 2220 may include at least one additional operation. Additional operations may include operation 3102.

Operation 3102 illustrates accepting an indication of an individual's asthma, presenting a prescribed administration schedule of an albuterol-dispensing collar therapy for the individual, and presenting a prescription for engagement of the individual with a virtual world experience configured to teach the individual a deep breathing technique. For example, as shown in FIGS. 18 through 21, accepter module 2002 and presenter module 2016 may accept an indication of an individual's asthma, present a prescribed administration schedule of an albuterol-dispensing collar therapy for the individual, and present a prescription for engagement of the individual with a virtual world experience configured to teach the individual a deep breathing technique. In some instances, accepter module 2002 may include a computer processor and/or input means, for example a keyboard, a touchscreen, a network connection, and/or a memory device. In some instances, presenter module 2016 may include a computer processor and/or a display device, such as a computer monitor and/or a printer.

Figure 32:
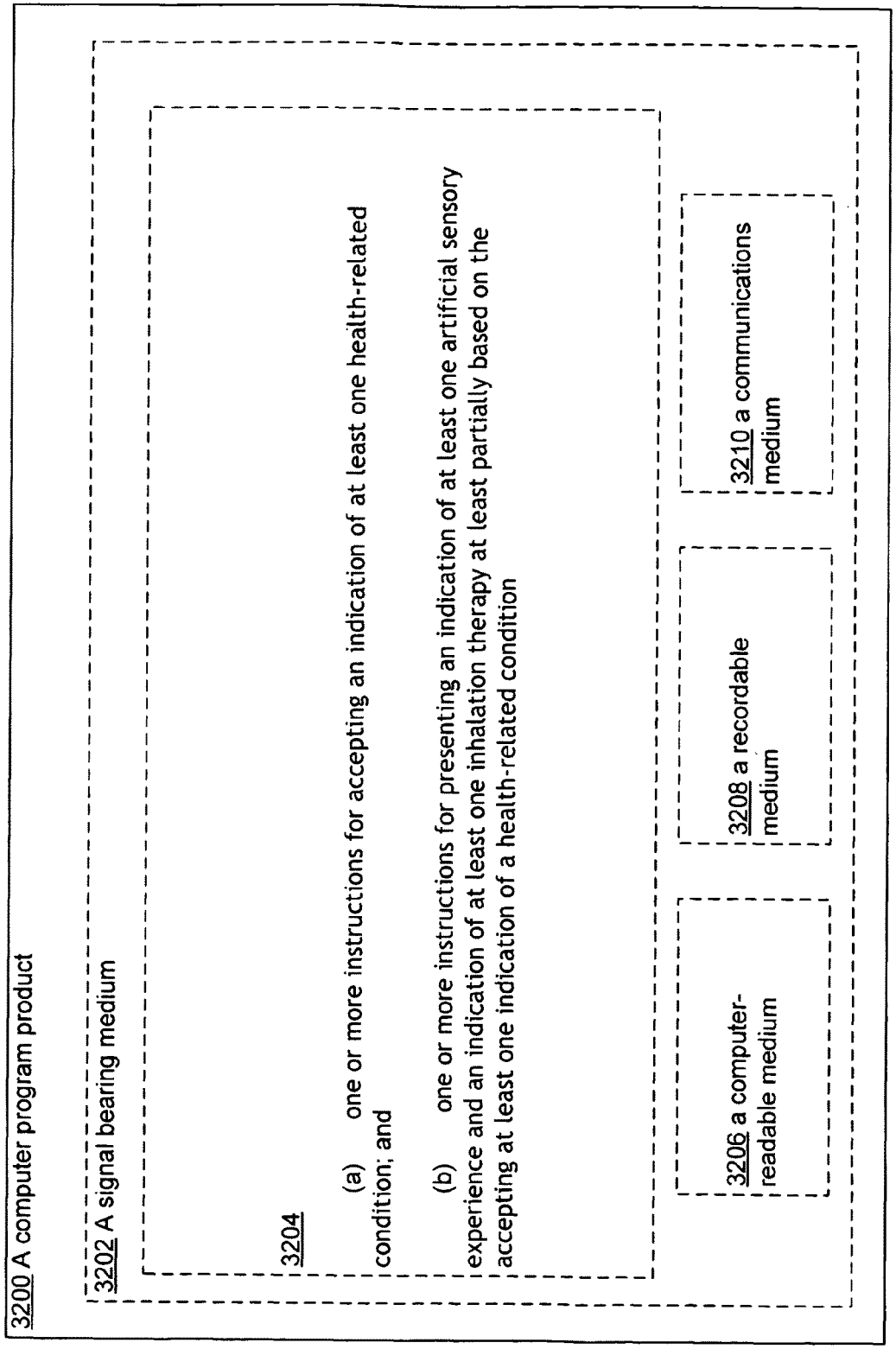
FIG. 32 illustrates a computer program product related to combining an inhaled bioactive agent and an artificial sensory experience.

FIG. 32 illustrates a partial view of an example computer program product 3200 that includes a computer program 3204 for executing a computer process on a computing device. An embodiment of the example computer program product 3200 is provided using a signal-bearing medium 3202, and may include one or more instructions for accepting an indication of at least one health-related condition and one or more instructions for presenting an indication of at least one artificial sensory experience and an indication of at least one inhalation therapy at least partially based on the accepting at least one indication of a health-related condition. The one or more instructions may be, for example, computer executable and/or logic-implemented instructions. In one implementation, the signal-bearing medium 3202 may include a computer-readable medium 3206. In one implementation, the signal bearing medium 3202 may include a recordable medium 3208. In one implementation, the signal bearing medium 3202 may include a communications medium 3210.

Figure 33:
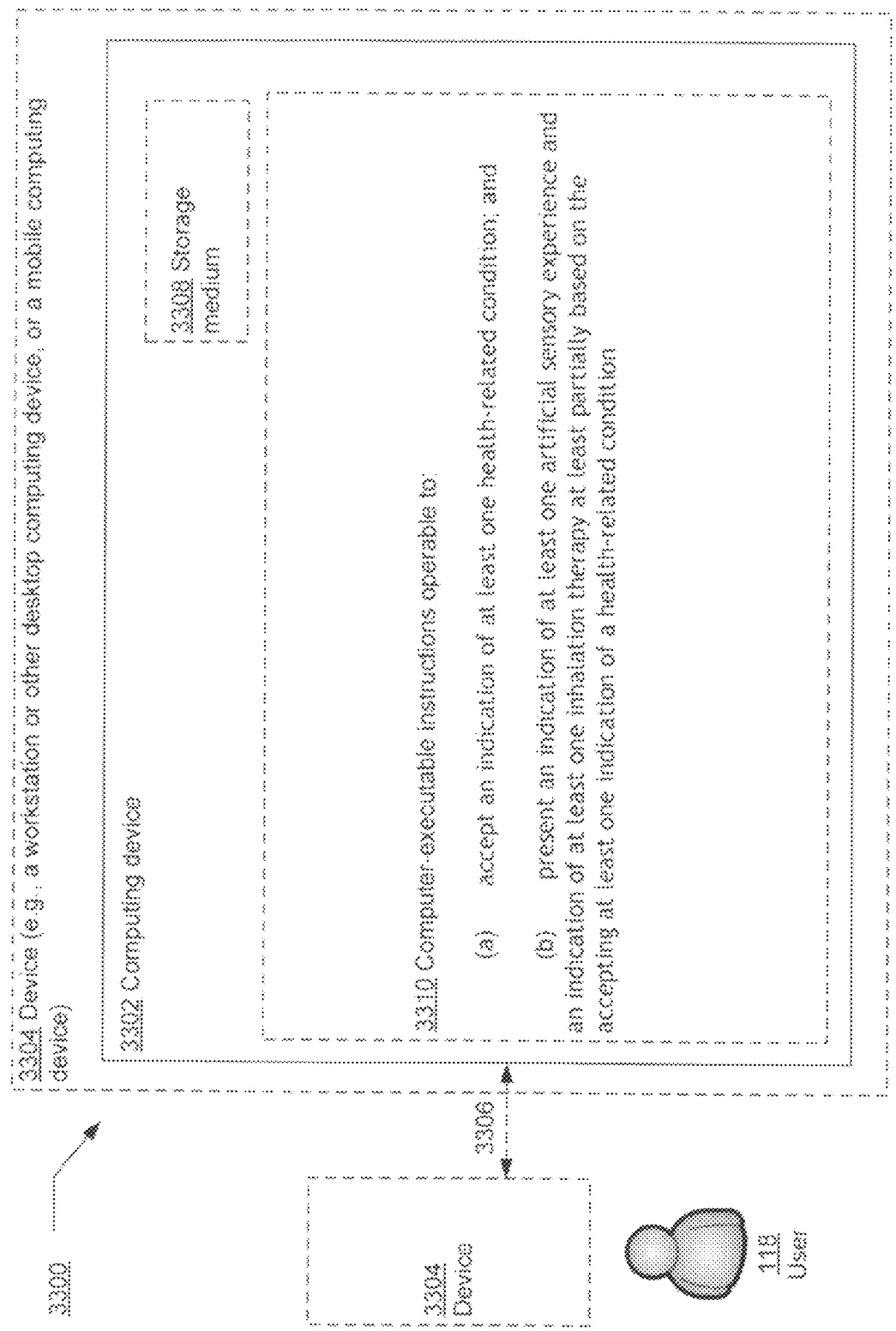
FIG. 33 illustrates a system related to combining an inhaled bioactive agent and an artificial sensory experience.

FIG. 33 illustrates an example system 3300 in which embodiments may be implemented. The system 3300 includes a computing system environment. The system 3300 also illustrates the user 118 using a device 3304, which is optionally shown as being in communication with a computing device 3302 by way of an optional coupling 3306. The optional coupling 3306 may represent a local, wide-area, or peer-to-peer network, or may represent a bus that is internal to a computing device (e.g., in example embodiments in which the computing device 3302 is contained in whole or in part within the device 3304). A storage medium 3308 may be any computer storage media.

The computing device 3302 includes computer-executable instructions 3310 that when executed on the computing device 3302 cause the computing device 3302 to accept an indication of at least one health-related condition and present an indication of at least one artificial sensory experience and an indication of at least one inhalation therapy at least partially based on the accepting at least one indication of a health-related condition. As referenced above and as shown in FIG. 33, in some examples, the computing device 3302 may optionally be contained in whole or in part within the device 3304.

In FIG. 33, then, the system 3300 includes at least one computing device (e.g., 3302 and/or 3304). The computer-executable instructions 3310 may be executed on one or more of the at least one computing device. For example, the computing device 3302 may implement the computer-executable instructions 3310 and output a result to (and/or receive data from) the computing device 3304. Since the computing device 3302 may be wholly or partially contained within the computing device 3304, the device 3304 also may be said to execute some or all of the computer-executable instructions 3310, in order to be caused to perform or implement, for example, various ones of the techniques described herein, or other techniques.

The device 3304 may include, for example, a portable computing device, workstation, or desktop computing device. In another example embodiment, the computing device 3302 is operable to communicate with the device 3304 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in tight of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art wilt also appreciate that examples of electro-mechanical systems include but are not limited to a variety of consumer electronics systems, medical devices, as well as other systems such as motorized transport systems, factory automation systems, security systems, and/or communication/computing systems.

Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   an accepter module configured to accept at least one indication of at least one health-related condition;
   a determiner module configured to determine at least one virtual world experience at least partially based on the at least one indication of at least one health-related condition; and
   a presenter module configured to present at least one indication associated with the at least one virtual world experience,
   wherein at least one of the accepter module, the determiner module, or the presenter module is at least partially implemented using hardware.

2. The system of claim 1, wherein the accepter module configured to accept at least one indication of at least one health-related condition comprises:
   a physical condition accepter module configured to accept at least one indication of at least one health-related physical condition.

3. The system of claim 1, wherein the presenter module configured to present at least one indication associated with the at least one virtual world experience comprises:
   a prescription presenter module configured to present at least one indication associated with at least one of one or more prescribed artificial sensory experiences or one or more prescribed inhalation therapies.

4. The system of claim 1, wherein the determiner module configured to determine at least one virtual world experience at least partially based on the at least one indication of at least one health-related condition comprises:
   an algorithm utilizer module configured to utilize at least one algorithm configured for recommending at least one of one or more artificial sensory experiences or one or more inhalation therapies.

5. The system of claim 1, wherein the determiner module configured to determine at least one virtual world experience at least partially based on the at least one indication of at least one health-related condition and the presenter module configured to present at least one indication associated with the at least one virtual world experience comprise:
   a presenter module configured to present an indication of at least one artificial sensory experience and an indication of at least one inhalation therapy at least partially based on accepting at least one indication of a health-related condition.

6. A computer-implemented method, comprising:
accepting at least one indication of at least one health-related condition;
determining at least one virtual world experience at least partially based on the at least one indication of at least one health-related condition; and
presenting at least one indication associated with the at least one virtual world experience,
wherein at least one of the accepting, determining, or presenting is at least partially implemented using hardware.

7. The computer-implemented method of claim 6, wherein accepting at least one indication of at least one health-related condition comprises:
accepting at least one indication of at least one health-related mental condition.

8. The computer-implemented method of claim 6, wherein determining at least one virtual world experience at least partially based on the at least one indication of at least one health-related condition comprises:
utilizing at least one algorithm configured for identifying at least one contraindication of at least one of one or more artificial sensory experiences or one or more inhalation therapies.

9. The computer-implemented method of claim 6, wherein presenting at least one indication associated with the at least one virtual world experience comprises:
presenting at least one indication associated with at least one of one or more virtual world experiences, one or more massively multiplayer online games, or one or more learning tutorials.

10. A system, comprising:
circuitry for accepting at least one indication of at least one health-related condition;
circuitry for determining at least one virtual world experience at least partially based on the at least one indication of at least one health-related condition; and
circuitry for presenting at least one indication associated with the at least one virtual world experience.

11. The system of claim 10, wherein the circuitry for accepting at least one indication of at least one health-related condition comprises:
circuitry for accepting at least one indication of at least one health-related condition based at least partially on at least one medical history.

12. The system of claim 10, wherein the circuitry for accepting at least one indication of at least one health-related condition comprises:
circuitry for accepting at least one indication of at least one health-related condition based at least partially on at least some user input.

13. The system of claim 12, wherein the circuitry for accepting at least one indication of at least one health-related condition based at least partially on at least some user input comprises:
circuitry for accepting at least one indication of at least one health-related condition from a health care professional.

14. The system of claim 12, wherein the circuitry for accepting at least one indication of at least one health-related condition based at least partially on at least some user input comprises:
circuitry for accepting at least one indication of at least one health-related condition from at least one of an affected individual, a patient, or a prospective patient.

15. The system of claim 10, wherein the circuitry for determining at least one virtual world experience at least partially based on the at least one indication of at least one health-related condition comprises:
circuitry for utilizing at least one algorithm configured for recommending at least one of one or more artificial sensory experiences or one or more inhalation therapies.

16. The system of claim 10, wherein the circuitry for presenting at least one indication associated with the at least one virtual world experience comprises:
circuitry for presenting at least one indication of at least one effect associated with at least one indication associated with at least one of one or more prescribed artificial sensory experiences or one or more prescribed inhalation therapies.

17. The system of claim 16, wherein the circuitry for presenting at least one indication of at least one effect associated with at least one indication associated with at least one of one or more prescribed artificial sensory experiences or one or more prescribed inhalation therapies comprises:
circuitry for presenting at least one indication of at least one expected desired effect associated with at least one of one or more prescribed artificial sensory experiences or one or more prescribed inhalation therapies.

18. The system of claim 16, wherein the circuitry for presenting at least one indication of at least one effect associated with at least one indication associated with at least one of one or more prescribed artificial sensory experiences or one or more prescribed inhalation therapies comprises:
circuitry for presenting at least one indication of at least one expected adverse effect associated with at least one of one or more prescribed artificial sensory experiences or one or more prescribed inhalation therapies.

19. The system of claim 10, wherein the circuitry for presenting at least one indication associated with the at least one virtual world experience comprises:
circuitry for presenting at least one indication associated with at least one prescribed inhalation therapy.

20. The system of claim 19, wherein the circuitry for presenting at least one indication associated with at least one prescribed inhalation therapy comprises:
circuitry for presenting at least one indication associated with at least one prescribed bioactive agent.

21. The system of claim 20, wherein the circuitry for presenting at least one indication associated with at least one prescribed bioactive agent comprises:
circuitry for presenting at least one indication associated with at least one time period of at least one expected change in bioactive agent effectiveness.

22. The system of claim 20, wherein the circuitry for presenting at least one indication associated with at least one prescribed bioactive agent comprises:
circuitry for presenting at least one indication associated with at least one time period of at least one expected change in bioactive agent blood concentration.

23. The system of claim 19, wherein the circuitry for presenting at least one indication associated with at least one prescribed inhalation therapy comprises:
circuitry for presenting at least one indication associated with at least one of a steroid, an anti-inflammatory, a bronchodilator, an expectorant, menthol, nitrous oxide, a CNS depressant, an anti-allergic agent, a muscle relaxant, or an anesthetic.

24. The system of claim 19, wherein the circuitry for presenting at least one indication associated with at least one prescribed inhalation therapy comprises:

circuitry for presenting at least one indication associated with at least one bioactive agent-dispensing device-based inhalation therapy.

25. The system of claim 10, wherein the circuitry for presenting at least one indication associated with the at least one virtual world experience comprises:
    circuitry for presenting at least one indication associated with at least one unregulated inhalation agent.

26. The system of claim 25, wherein the circuitry for presenting at least one indication associated with at least one unregulated inhalation agent comprises:
    circuitry for presenting at least one indication associated with at least one recreational inhalation agent.

27. The system of claim 26, wherein the circuitry for presenting at least one indication associated with at least one recreational inhalation agent comprises:
    circuitry for presenting at least one indication associated with at least one aromatherapy.

28. The system of claim 10, wherein the circuitry for presenting at least one indication associated with the at least one virtual world experience comprises:
    circuitry for presenting one or more of at least one indication of at least one artificial sensory experience or at least one indication of at least one inhalation therapy at least partly based on at least one personal medical history.

29. The system of claim 10, wherein the circuitry for presenting at least one indication associated with the at least one virtual world experience comprises:
    circuitry for presenting one or more of at least one indication of at least one artificial sensory experience or at least one indication of at least one inhalation therapy at least partly based on at least some experimental data.

30. The system of claim 10, wherein the circuitry for presenting at least one indication associated with the at least one virtual world experience comprises:
    circuitry for presenting one or more of at least one indication of at least one artificial sensory experience or at least one indication of at least one inhalation therapy at least partly based on at least one medical reference tool.

31. The system of claim 10, wherein the circuitry for presenting at least one indication associated with the at least one virtual world experience comprises:
    circuitry for presenting the at least one indication to at least one output device.

32. The system of claim 31, wherein the circuitry for presenting the at least one indication to at least one output device comprises:
    circuitry for presenting the at least one indication to at least one user interface.

33. The system of claim 31, wherein the circuitry for presenting the at least one indication to at least one output device comprises:
    circuitry for presenting the at least one indication to at least one mobile device.

34. The system of claim 10, wherein the circuitry for presenting at least one indication associated with the at least one virtual world experience comprises:
    circuitry for presenting the at least one indication to at least one third party.

35. The system of claim 34, wherein the circuitry for presenting the at least one indication to at least one third party comprises:
    circuitry for presenting the at least one indication to at least one health care provider.

36. The system of claim 34, wherein the circuitry for presenting the at least one indication to at least one third party comprises:
    circuitry for selectively presenting the at least one indication only to at least one individual associated with the at least one health-related condition.

* * * * *